(12) United States Patent
Nakao et al.

(10) Patent No.: US 11,231,436 B2
(45) Date of Patent: Jan. 25, 2022

(54) FLOW RATE MEASURING METHOD, FLOW RATE MEASURING DEVICE, AND PROGRAM

(71) Applicants: Sony Corporation, Tokyo (JP); Sony Semiconductor Solutions Corporation, Kanagawa (JP)

(72) Inventors: Isamu Nakao, Kanagawa (JP); Noriyuki Kishii, Kanagawa (JP); Tetsuro Kuwayama, Tokyo (JP); Kensei Jo, Tokyo (JP)

(73) Assignees: SONY CORPORATION, Tokyo (JP); SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 263 days.

(21) Appl. No.: 16/608,187

(22) PCT Filed: Feb. 16, 2018

(86) PCT No.: PCT/JP2018/005452
§ 371 (c)(1),
(2) Date: Oct. 25, 2019

(87) PCT Pub. No.: WO2018/203429
PCT Pub. Date: Nov. 8, 2018

(65) Prior Publication Data
US 2021/0102969 A1 Apr. 8, 2021

(30) Foreign Application Priority Data
May 2, 2017 (JP) .............................. JP2017-091881

(51) Int. Cl.
*G01P 5/22* (2006.01)
*A61B 5/026* (2006.01)
(Continued)

(52) U.S. Cl.
CPC .............. *G01P 5/22* (2013.01); *A61B 5/0261* (2013.01); *G01P 5/26* (2013.01); *G01P 13/045* (2013.01)

(58) Field of Classification Search
CPC . G01P 5/22; G01P 5/26; G01P 13/045; A61B 5/0261
(Continued)

(56) References Cited

U.S. PATENT DOCUMENTS

2012/0277559 A1 11/2012 Kohl-Bareis et al.

FOREIGN PATENT DOCUMENTS

| JP | 1-124437 A | 5/1989 |
|----|------------|--------|
| JP | 10-314118 A | 12/1998 |

(Continued)

OTHER PUBLICATIONS

International Search Report and Written Opinion dated May 1, 2018 for PCT/JP2018/005452 filed on Feb. 16, 2018, 8 pages pages including English Translation of the International Search Report.

*Primary Examiner* — Daniel L Murphy
(74) *Attorney, Agent, or Firm* — Xsensus LLP

(57) ABSTRACT

The flow rate of light scattering fluid is measured more easily and at a higher speed.
A flow rate measuring method according to the present disclosure includes: generating two or more speckle images by continually imaging light scattering fluid to be measured, while defining time shorter than spatial correlation disappearance time corresponding to time in which spatial correlation between speckle patterns generated by the light scattering fluid disappears as exposure time, at a time interval shorter than the spatial correlation disappearance time; and calculating direction and speed of flow of the light scattering fluid from time variation of the speckle patterns between the two or more speckle images, in which the
(Continued)

speckle images are imaged by using an imaging device mounted with an area sensor and a pixel group of a part of the area sensor or by using an imaging device mounted with a line sensor.

9 Claims, 15 Drawing Sheets

(51) Int. Cl.
  *G01P 13/04* (2006.01)
  *G01P 5/26* (2006.01)

(58) Field of Classification Search
  USPC .......................................................... 356/28
  See application file for complete search history.

(56) References Cited

FOREIGN PATENT DOCUMENTS

| | | |
|---|---|---|
| JP | 2003-180641 A | 7/2003 |
| JP | 2005-515818 A | 6/2005 |
| JP | 2010-055064 A | 3/2010 |
| JP | 2016-005525 A | 1/2016 |

FLOW RATE MEASURING METHOD, FLOW RATE MEASURING DEVICE, AND PROGRAM

CROSS-REFERENCE TO RELATED APPLICATIONS

The present application is based on PCT filing PCT/JP2018/005452, filed Feb. 16, 2018, which claims priority to JP 2017-091881, filed May 2, 2017, the entire contents of each are incorporated herein by reference.

TECHNICAL FIELD

The present disclosure relates to a flow rate measuring method, a flow rate measuring device, and a program.

BACKGROUND ART

In the medical field, for example, the flow of fluid such as blood is sometimes required to be detected during treatment. For example, the following Patent Document 1 discloses a liquid analyzing device for gaining insights on such fluid. The liquid analyzing device uses time variation of a laser speckle.

CITATION LIST

Patent Document

Patent Document 1: Japanese Patent Application Laid-Open No. 2016-5525

SUMMARY OF THE INVENTION

Problems to be Solved by the Invention

In a device, as disclosed in the above Patent Document 1, using time variation of a laser speckle, physical quantities are used as an index reflecting the magnitude of flow. The physical quantities include, for example, speckle contrast in time space, correlation time of intensity variation of a speckle image, and entropy. The speckle contrast is obtained by dividing the standard deviation of the optical signal intensity in the speckle image by the average value of the optical signal intensity.

A speckle image is different from a typical image. The speckle image is obtained by imaging a random diffraction/interference phenomenon caused by the fine structure of an object of interest. Consequently, in a case where the object of interest moves sufficiently larger than the wavelength of light, a speckle image generated by the object has completely different patterns before and after the movement. Meanwhile, in a case where the object translates a slight distance of nearly a wavelength of light without change in shape, a movement distance and a movement direction can be identified from the speckle image since the pattern of the speckle image is held.

The fine shape of a light scattering fluid, such as blood and lymph, in a living body is continuously changed by, for example, convection, turbulence, and/or Brownian motion. The fine shape of such light scattering fluid changes at high speed in, for example, one millisecond or less depending on, for example, a diffusion coefficient, temperature, and viscosity. A speckle pattern changes at a similar speed. Consequently, in order to detect the flow rate and the flow direction, the second and subsequent speckle images for calculating the physical quantities as described above are required to be captured before the shape of the object (fluid) changes.

For example, in order to image an object whose shape changes in one millisecond twice or more before change in shape, high-speed imaging at, for example, 10 kfps or more is required to be achieved. An imaging element used for ordinary imaging of a moving image, however, has a frame rate of 60 fps. An imaging element of ordinary type has a limit of high-speed capturing at only approximately one kfps. Some cameras can perform capturing at a speed higher than such a frame rate. Unfortunately, these cameras have limits in capturing time, or are expensive. If the cameras are intended to be easily used in, for example, clinical practice, great restrictions are laid in the current situation.

Consequently, in view of the above-described circumstances, the present disclosure proposes a flow rate measuring method, a flow rate measuring device, and a program that are capable of measuring the flow rate of light scattering fluid more easily and at a higher speed.

Solutions to Problems

According to the present disclosure, there is provided a flow rate measuring method including: generating two or more speckle images by continually imaging light scattering fluid to be measured, while defining time shorter than spatial correlation disappearance time corresponding to time in which spatial correlation between speckle patterns generated by the light scattering fluid disappears as exposure time, at a time interval shorter than the spatial correlation disappearance time; and calculating direction and velocity of flow of the light scattering fluid from time variation of the speckle patterns between the two or more speckle images, in which the speckle images are imaged by using an imaging device mounted with an area sensor and a pixel group of a part of the area sensor or by using an imaging device mounted with a line sensor.

Furthermore, according to the present disclosure, there is provided a flow rate measuring device including: a laser light source configured to apply a predetermined wavelength of laser light to light scattering fluid to be measured; an imaging device configured to generate two or more speckle images by continually imaging the light scattering fluid, while defining time shorter than spatial correlation disappearance time corresponding to time in which spatial correlation between speckle patterns generated by the light scattering fluid disappears as exposure time, at a time interval shorter than the spatial correlation disappearance time; and an arithmetic processing unit configured to calculate direction and speed of flow of the light scattering fluid from time variation of the speckle patterns between the two or more speckle images, in which the speckle images are imaged by using an imaging device mounted with an area sensor as the imaging device and a pixel group of a part of the area sensor or by using an imaging device mounted with a line sensor as the imaging device.

Furthermore, according to the present disclosure, there is provided a flow rate measuring device including an arithmetic processing unit configured to calculate direction and speed of flow of light scattering fluid from time variation of speckle patterns between two or more speckle images by using the two or more speckle images generated by continually imaging the light scattering fluid to be measured on which a predetermined wavelength of laser light is applied, while defining time shorter than spatial correlation disappearance time corresponding to time in which spatial correlation between the speckle patterns generated by the light scattering fluid disappears as exposure time, at a time interval shorter than the spatial correlation disappearance time, in which the arithmetic processing unit uses objects, as the two or more speckle images, imaged by using an imaging device mounted with an area sensor and a pixel group of a part of the area sensor or by using an imaging device mounted with a line sensor.

Furthermore, according to the present disclosure, there is provided a program causing a computer to implement an arithmetic processing function of calculating direction and speed of flow of light scattering fluid from time variation of speckle patterns between two or more speckle images by using the two or more speckle images generated by continually imaging light scattering fluid to be measured on which a predetermined wavelength of laser light is applied, while defining time shorter than spatial correlation disappearance time corresponding to time in which spatial correlation between the speckle patterns generated by the light scattering fluid disappears as exposure time, at a time interval shorter than the spatial correlation disappearance time, in which the arithmetic processing function uses objects, as the two or more speckle images, imaged by using an imaging device mounted with an area sensor and a pixel group of a part of the area sensor or by using an imaging device mounted with a line sensor.

According to the present disclosure, two or more speckle images are generated by continually imaging light scattering fluid to be measured, while defining time shorter than spatial correlation disappearance time corresponding to time in which spatial correlation between the speckle patterns generated by the light scattering fluid disappears as exposure time, at a time interval shorter than the spatial correlation disappearance time. These speckle images are imaged by using an imaging device mounted with an area sensor and a pixel group of a part of the area sensor or by using an imaging device mounted with a line sensor. The direction and speed of flow of the light scattering fluid are calculated from time variation of the speckle patterns between the two or more obtained speckle images.

Effects of the Invention

As described above, according to the present disclosure, the flow rate of light scattering fluid can be measured more easily and at a higher speed.

Note that the above-described effects are not necessarily limitative, and any of the effects indicated in the specification or other effects that can be grasped from the specification may be produced together with or in place of the above-described effects.

MODE FOR CARRYING OUT THE INVENTION

A preferred embodiment of the present disclosure will now be described in detail with reference to the accompanying drawings. Note that, in the present specification and the drawings, components having substantially the same functional configuration are denoted by the same signs, and redundant description thereof will be omitted.

Note that the description will be given in the following order.
1. First Embodiment
1.1. Flow Rate Measuring Method
1.2. Flow Rate Measuring Device
2. Example

First Embodiment

<Flow Rate Measuring Method>

First, a flow rate measuring method according to a first embodiment of the present disclosure will be described in detail with reference to FIGS. 1 to 9.

Figure 1:
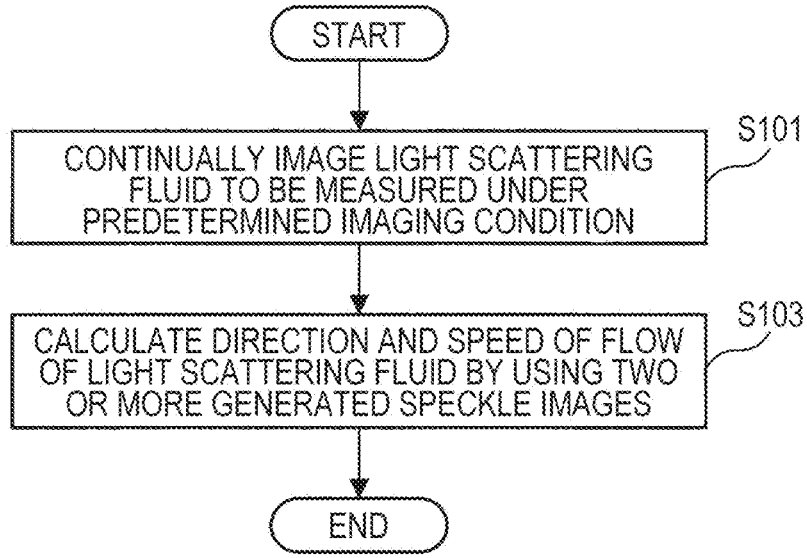
FIG. 1 is a flow chart illustrating one example of the flow of a flow rate measuring method according to an embodiment of the present disclosure.
Figure 2:
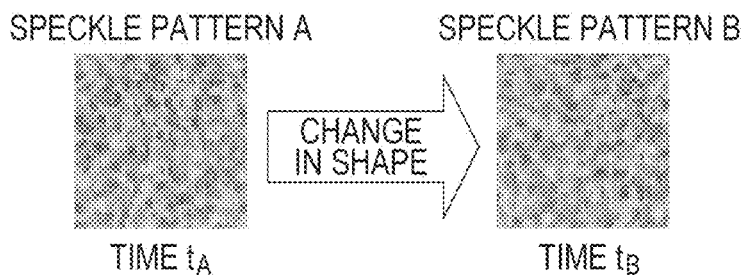
FIG. 2 is an explanatory view for illustrating time variation of a speckle pattern.
Figure 3:
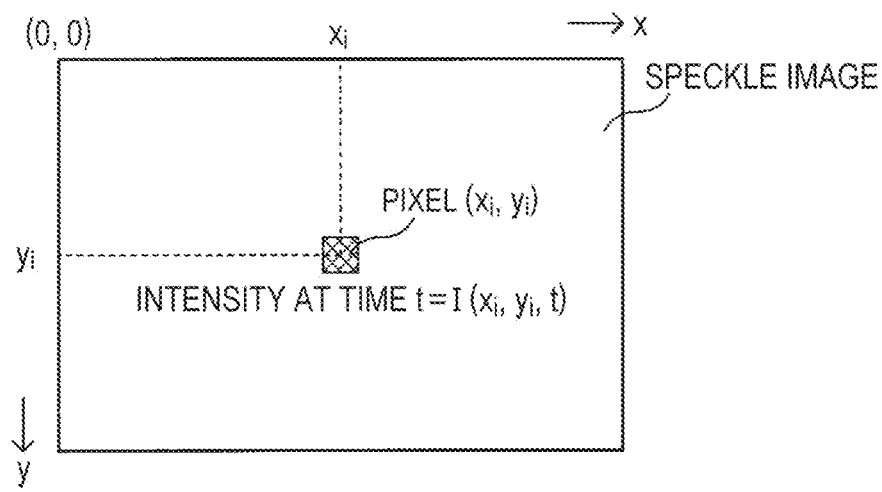
FIG. 3 is an explanatory view for illustrating a speckle image.
Figure 4:
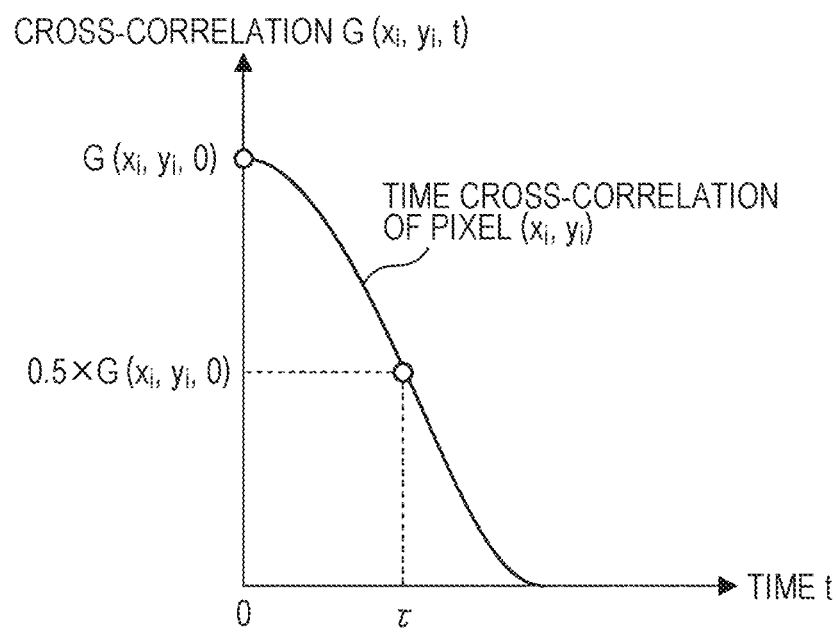
FIG. 4 is an explanatory view for illustrating spatial correlation disappearance time.
Figure 5:
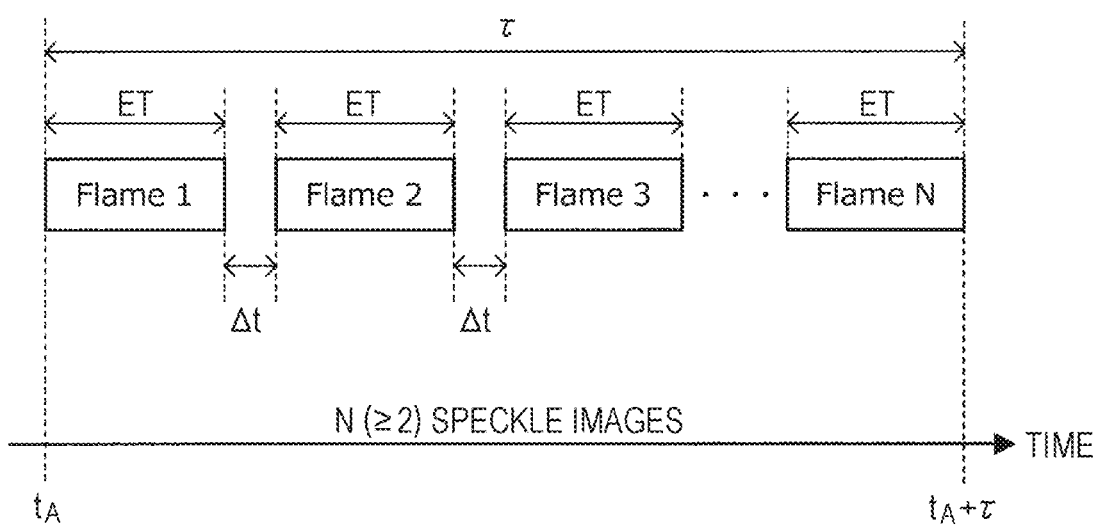
FIG. 5 is an explanatory view for illustrating an imaging condition in the flow rate measuring method according to the same embodiment.
Figure 6A:
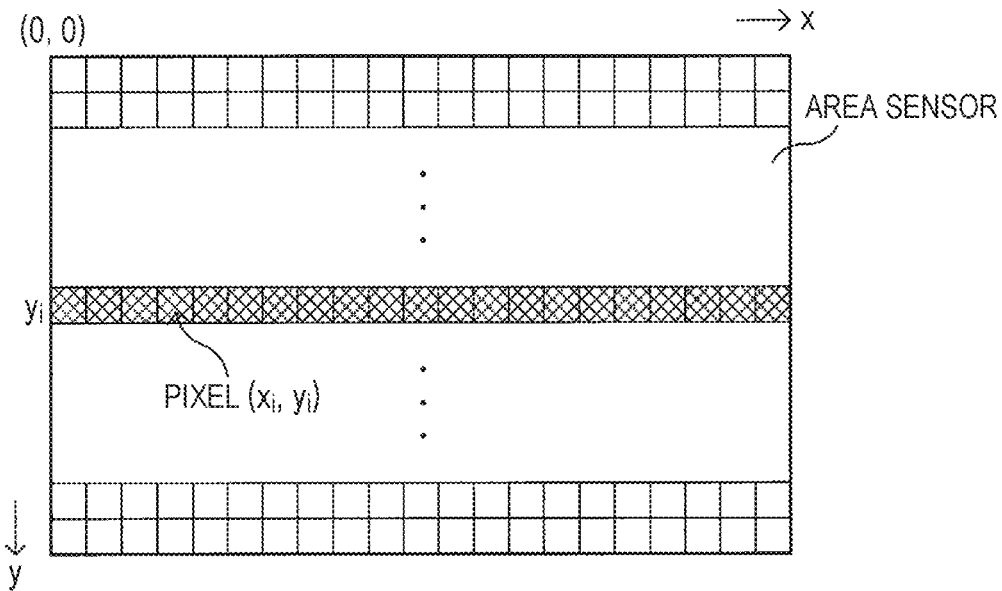
FIG. 6A is an explanatory view for illustrating an imaging element used in the flow rate measuring method according to the same embodiment.
Figure 6B:
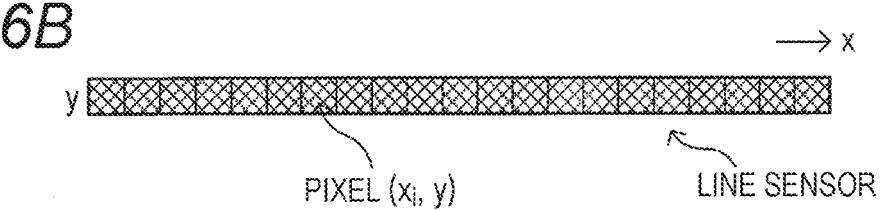
FIG. 6B is an explanatory view for illustrating the imaging element used in the flow rate measuring method according to the same embodiment.
Figure 7:
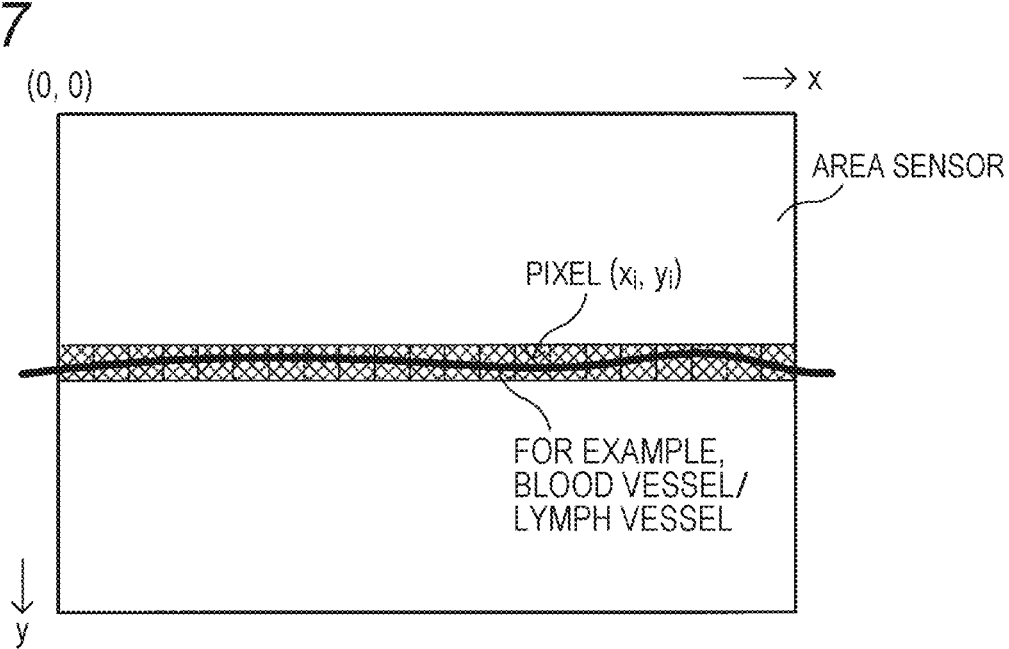
FIG. 7 is an explanatory view for illustrating the flow rate measuring method according to the same embodiment.
Figure 8:
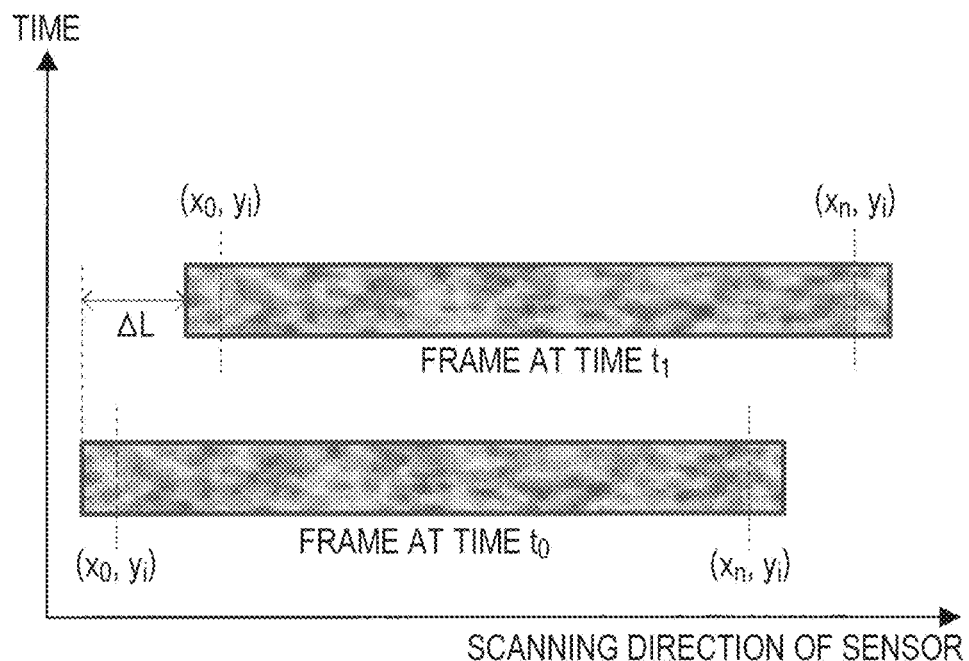
FIG. 8 is an explanatory view for illustrating the flow rate measuring method according to the same embodiment.
Figure 9:
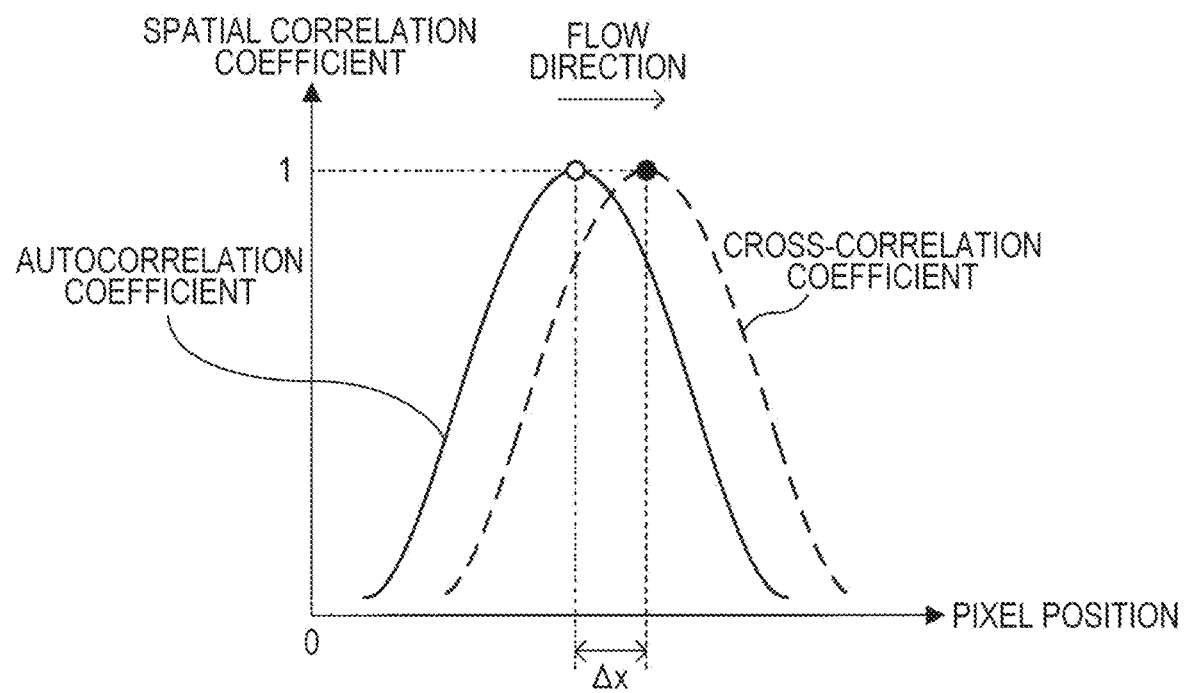
FIG. 9 is an explanatory view for illustrating the flow rate measuring method according to the same embodiment.

FIG. 1 is a flow chart illustrating one example of the flow of the flow rate measuring method according to the embodiment. FIG. 2 is an explanatory view for illustrating time variation of a speckle pattern. FIG. 3 is an explanatory view for illustrating a speckle image. FIG. 4 is an explanatory view for illustrating spatial correlation disappearance time. FIG. 5 is an explanatory view for illustrating an imaging condition in the flow rate measuring method according to the embodiment. FIGS. 6A and 6B are explanatory views for illustrating an imaging element used in the flow rate measuring method according to the embodiment. FIGS. 7 to 9 are explanatory views for illustrating the flow rate measuring method according to the embodiment.

As previously mentioned, in a case where light scattering fluid to be measured translates a slight distance of nearly a wavelength of light without change in shape, a movement distance and a movement direction can be identified from a plurality of speckle images in which a speckle pattern is held. For this purpose, imaging at a high frame rate is important since imaging a plurality of speckle images at high speed prior to change in shape of the light scattering fluid is required.

The inventor earnestly considered a method of imaging a speckle image more easily at a high frame rate as described above. As a result, the inventor found that continually imaging light scattering fluid to be measured under a predetermined imaging condition enables imaging a speckle image at high frame rate more easily, and completed a flow rate measuring method described in detail below.

As schematically illustrated in FIG. 1, the flow rate measuring method according to the embodiment includes an imaging step (S101) and an arithmetic processing step (S103). In the imaging step S101, light scattering fluid to be measured is continually imaged under a predetermined imaging condition. In the arithmetic processing step S103, the direction and speed of flow of the light scattering fluid is calculated by using two or more speckle images generated in the imaging step.

Here, the light scattering fluid in the embodiment means an object flowing through a predetermined flow path while scattering applied light. For example, such light scattering fluid includes, but is not particularly limited to, body fluids such as blood and lymph flowing in, for example, blood vessel and lymph vessel in a living body. Although, in the following description, body fluid such as blood and lymph flowing in, for example, a blood vessel and a lymph vessel in a living body is taken as one example of an object to be measured, the light scattering fluid according to the embodiment is not limited to such an example.

[Imaging Step S101]

As previously mentioned, a speckle image is different from a typical image. The speckle image is obtained by imaging a random diffraction/interference phenomenon caused by the fine structure of an object of interest. Furthermore, the fine shape of light scattering fluid, such as blood and lymph, in a living body is continuously changed by, for example, convection, turbulence, and/or Brownian motion. The fine shape of such light scattering fluid changes at high speed in, for example, one millisecond or less (approximately 10 to 100 microseconds in a case of blood) depending on, for example, a diffusion coefficient, temperature, and viscosity. A speckle pattern changes at a similar speed. Consequently, for example, as schematically illustrated in FIG. 2, a speckle pattern A and a speckle pattern B are different from each other. The speckle pattern A has been observed at a time point $t_A$. The speckle pattern B has been observed at a time point $t_B$ after time, in which the shape of the light scattering fluid changes, had passed. In other words, in the speckle pattern A and the speckle pattern B illustrated in FIG. 2, the spatial correlation between both of the speckle patterns is absent.

First, the time until a speckle pattern is not held due to change in shape of light scattering fluid (i.e., time until spatial correlation between speckle patterns disappears) will be considered below. The "time until spatial correlation between speckle patterns disappears" will hereinafter be referred to as "spatial correlation disappearance time".

FIG. 3 schematically illustrates an image obtained by imaging a speckle pattern (hereinafter also referred to as a "speckle image") of light scattering fluid. The light scattering fluid is linearly illuminated with laser light emitted from a predetermined laser light source. A plurality of pixels constitutes each of an x direction and a y direction of the image. Furthermore, the position in the upper left of the image is defined as the origin (0, 0) of the coordinate system indicating pixel positions. Any pixel position is represented as $(x_i, y_i)$. Moreover, the intensity (signal intensity) of a pixel $(x_i, y_i)$ of interest at a time point t is represented as $I(x_i, y_i, t)$.

In a case of considering the position of light scattering fluid of interest as fixed, a speckle pattern of the light scattering fluid at a position changes over time. As schematically illustrated in FIG. 4, the signal intensity $I(x_i, y_i, t)$ of a speckle pattern at a pixel position $(x_i, y_i)$ attenuates over time. In the case, the correlation (time correlation) $G_t$ between two kinds of speckle patterns at two time points can be expressed by the following expression (101).

[math 1]

$$G_t(x,y,\tau)=\int I(x,y,t)I(x,y,t+\tau)dt \qquad \text{Expression (101)}$$

In the embodiment, the time, in which the time correlation $G_t(x, y, \tau)=0.5\times G_t(x, y, 0)$ holds, (i.e., time required until the time correlation attenuates to half an initial value) $\tau$, calculated by the above-described expression (101) is defined as the above-described spatial correlation disappearance time.

In order to measure the flow rate (i.e., direction and speed of flow) of the light scattering fluid, using speckle patterns at two or more time points is required. As described above, since a speckle pattern is held without time variation within the spatial correlation disappearance time, it is sufficient if the light scattering fluid is imaged twice or more within the spatial correlation disappearance time T to generate two or more speckle images.

Consequently, in the imaging step S101 according to the embodiment, as schematically illustrated in FIG. 5, time shorter than the spatial correlation disappearance time $\tau$ is defined as an exposure time (ET). The light scattering fluid is continually imaged at a time interval $\Delta t$ shorter than the spatial correlation disappearance time τ to generate speckle images of N frames or more (N≥2, i.e., N sheets or more).

Here, the specific length of the spatial correlation disappearance time τ can be specified in advance by actually observing the time variation of the speckle pattern of the light scattering fluid to be measured. Furthermore, the specific length of the exposure time ET schematically illustrated in FIG. 5 is not particularly limited, and is appropriately only required to set in accordance with the brightness of the speckle pattern under an imaging environment and, for example, the performance of, for example, equipment to be used. Similarly, the imaging interval Δt schematically illustrated in FIG. 5 is not particularly limited, and is appropriately only required to set in accordance with, for example, the performance of, for example, equipment to be used.

In order to achieve imaging at a high-speed frame rate as illustrated in FIG. 5, an imaging device in which a sensor as illustrated in FIG. 6A or 6B is mounted is used in the flow rate measuring method according to the embodiment. For example, FIG. 6A schematically illustrates an imaging device mounted with an area sensor that includes a plurality of pixels ($x_i$, $y_i$). That is, in a case where the imaging device is used, and scanning is performed with all pixels constituting the area sensor, imaging under the imaging condition as illustrated in FIG. is likely to be difficult. Consequently, in a case where an imaging device mounted with an area sensor is used, a speckle image is captured by using a pixel group of a part of the area sensor. Scanning a speckle pattern not with all pixels but with only the pixel group of a part enables extremely high speed scanning compared to scanning with all the pixels. As a result, imaging at a high-speed frame rate can be achieved. For example, in the example illustrated in FIG. 6A, a speckle image is captured with a pixel group provided in the vicinity of the center of the area sensor.

Here, a plurality of pixel groups is preferably used for imaging the speckle pattern. The pixel groups are arranged in a direction parallel to the scanning direction of the area sensor (i.e., data reading direction in the area sensor).

Furthermore, the position, in the area sensor, of the pixel group used for capturing a speckle image is not particularly limited. The pixel group may be positioned in the vicinity of the center of the area sensor as illustrated in FIG. 6A, or at a place other than the center.

Furthermore, for example, an imaging device mounted with a line sensor as schematically illustrated in 6B can be used instead of the area sensor as schematically illustrated in FIG. 6A.

Note that, although FIGS. 6A and 6B illustrate one line of pixel group used for generating the speckle image, the line number of the sensor used for generating the speckle image is not limited to one, and a plurality of lines may be used within a range in which the imaging condition as illustrated in FIG. 5 can be achieved.

Light scattering fluid to be measured moves inside a conduit, such as a blood vessel and a lymph vessel, for example, extending in a predetermined direction. For example, as schematically illustrated in FIG. 7, imaging is preferably performed with the scanning direction of a sensor used for imaging being largely overlapped with the extending direction of the conduit (e.g., blood vessel and lymph vessel) (more particularly, with the conduit, through which the light scattering fluid flows, being largely positioned above the sensor pixel group used for imaging). This enables the light scattering fluid to be an imaging target in more pixel groups used for capturing a speckle image, and the flow rate of the light scattering fluid to be measured more accurately.

[Arithmetic Processing Step S103]

An arithmetic processing step performed by using two or more generated speckle images will now be described.

A plurality of speckle images is obtained by performing imaging under the imaging condition as schematically illustrated in FIG. 5, and each of the speckle images has substantially the same speckle patterns. Consequently, as schematically illustrated in FIG. 8, two speckle images captured at each of time points $t_0$ and $t_1$ within the spatial correlation disappearance time τ have deep similarities, and are constituted by the same number of pixels. Meanwhile, the speckle image at the time point $t_1$ shifts by ΔL from the speckle image at the time point $t_0$ in a flow direction of light scattering fluid. The direction and speed of flow of the light scattering fluid can be calculated by focusing on the shift direction and shift amount ΔL.

In the arithmetic processing step according to the embodiment, the cross-correlation between spatial distributions of the speckle images calculated by using two or more speckle patterns is preferably used as an index representing such time variation of the speckle patterns accompanying movement of the light scattering fluid. In addition, the direction and speed of flow of the light scattering fluid is preferably calculated on the basis of the cross-correlation between the spatial distributions of the speckle images.

Speckles of the light scattering fluid changes over time. Even in a case where sampling is performed on the same pixel, a speckle pattern slightly changes between adjacent frames as schematically illustrated in FIG. 8. In the case, the cross-correlation (spatial cross-correlation) between the spatial distributions of the speckle images of frames 0 and 1 can be expressed as in the following expression (103). Here, G (ξ, y, t) represents a correlation coefficient.

[math 2]

$$G(\xi,y,t)=\int I(x,y,t_0)I(x+\xi,y,t_1)dx \qquad \text{Expression (103)}$$

As described above, in a case where a plot of a spatial autocorrelation coefficient of the speckle image at the time point $t_0$ is set as a standard, the plot of a spatial cross-correlation coefficient of the speckle image at the time point $t_0$ and the speckle image at the time point $t_1$ shifts in a certain direction by a predetermined amount Δx as schematically illustrated in FIG. 9. In the flow rate measuring method according to the embodiment, the shift direction of the peak value of the spatial cross-correlation coefficient in the speckle image can be regarded as the flow direction of the light scattering fluid.

Furthermore, speed of the light scattering fluid can be calculated by using a shift amount Δx of the obtained peak value, the pixel size of a sensor, and the imaging time interval Δt. That is, the size corresponding to the shift amount Δx in object space can be calculated as a product of the shift amount Δx on the image surface and an image magnification. Meanwhile, the time required for the light scattering fluid to move the size in the object space can be specified by using an imaging order (what number of frames have been used) of a speckle image of interest and the imaging interval Δt of the speckle image. Speed of the light scattering fluid of interest can be calculated by using these values.

Note that a method of specifying the flow rate of light scattering fluid is not limited to the above-described method in which the spatial cross-correlation attracts attention. Any other method can be appropriately used.

The flow rate measuring method according to the embodiment has been described in detail above.

<Flow Rate Measuring Device>

A flow rate measuring device according to the embodiment will now be described in detail with reference to FIGS. 10 to 18. The flow rate measuring method as described above can be achieved with the flow rate measuring device.

Figure 10:
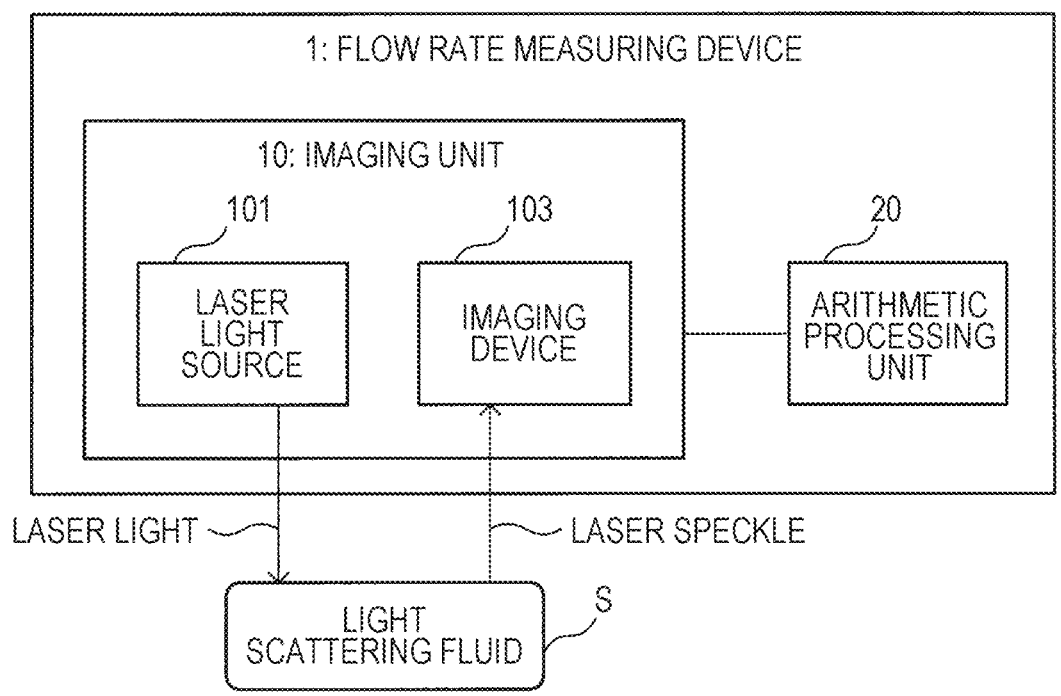
FIG. 10 is a block diagram schematically illustrating one example of the configuration of a flow rate measuring device according to the same embodiment.
Figure 11:
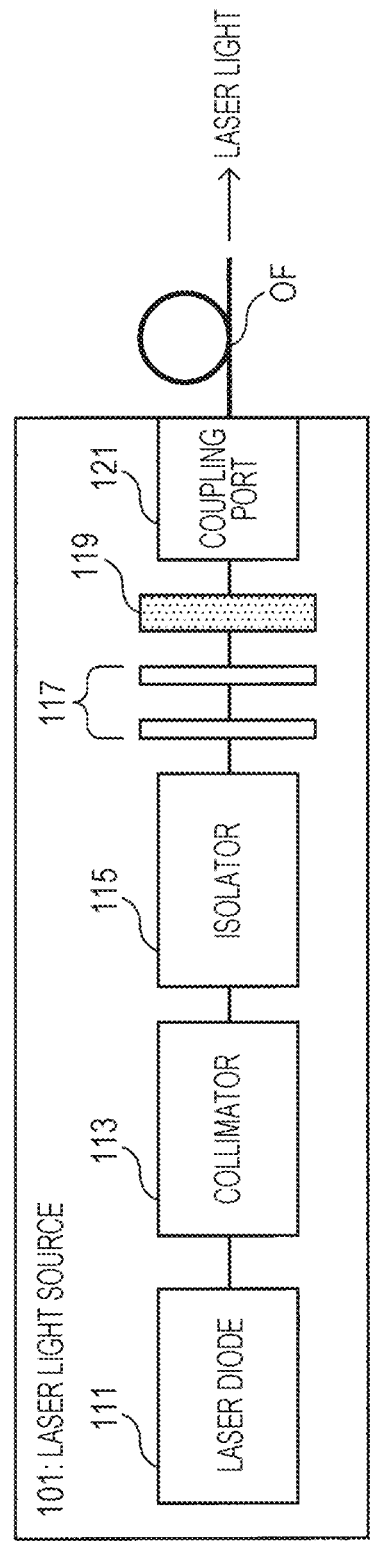
FIG. 11 is a block diagram schematically illustrating one example of the configuration of a laser light source provided in the flow rate measuring device according to the same embodiment.
Figure 12:
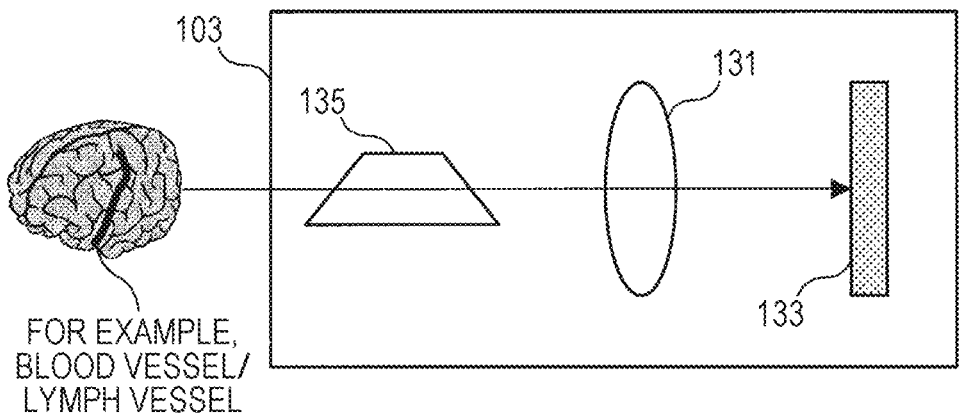
FIG. 12 is a block diagram schematically illustrating one example of the configuration of an imaging device provided in the flow rate measuring device according to the same embodiment.
Figure 13A:
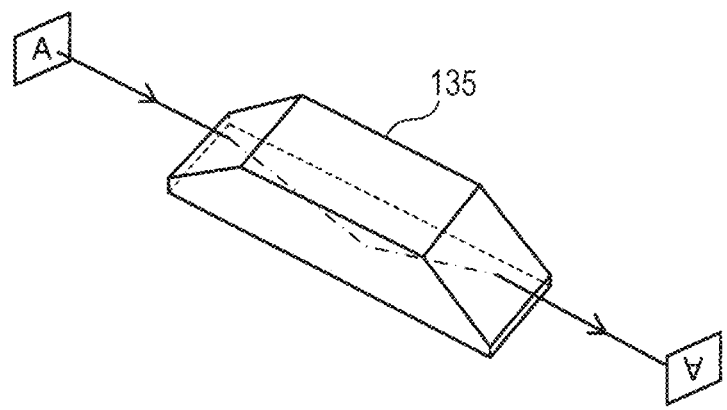
FIG. 13A is an explanatory view for illustrating a dove prism.
Figure 13B:
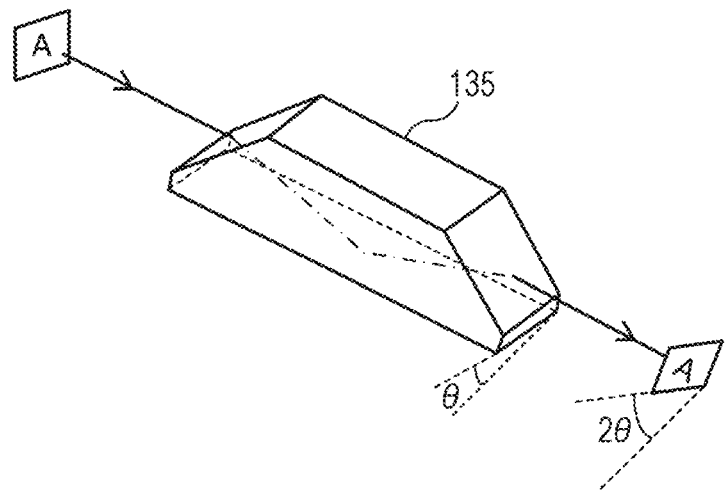
FIG. 13B is an explanatory view for illustrating the dove prism.
Figure 14:
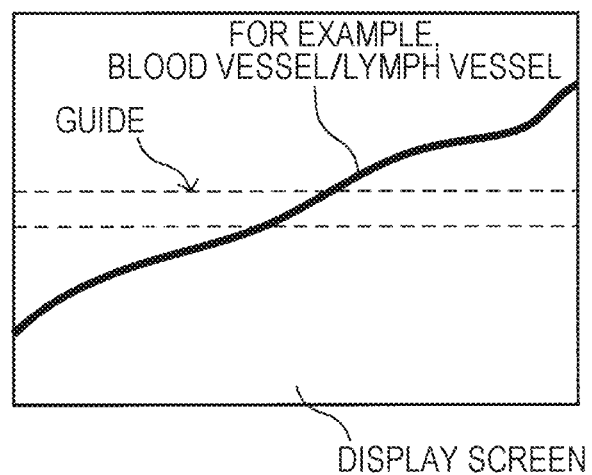
FIG. 14 is an explanatory view for illustrating the flow rate measuring device according to the same embodiment.
Figure 15:
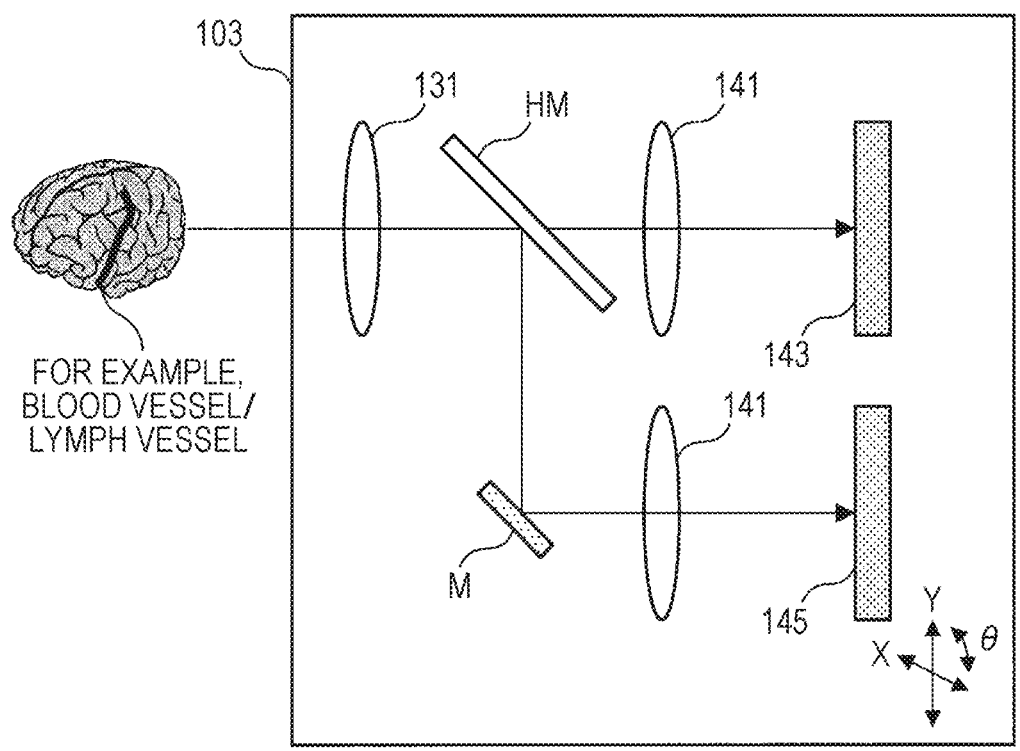
FIG. 15 is a block diagram schematically illustrating another example of the configuration of the imaging device provided in the flow rate measuring device according to the same embodiment.
Figure 16:
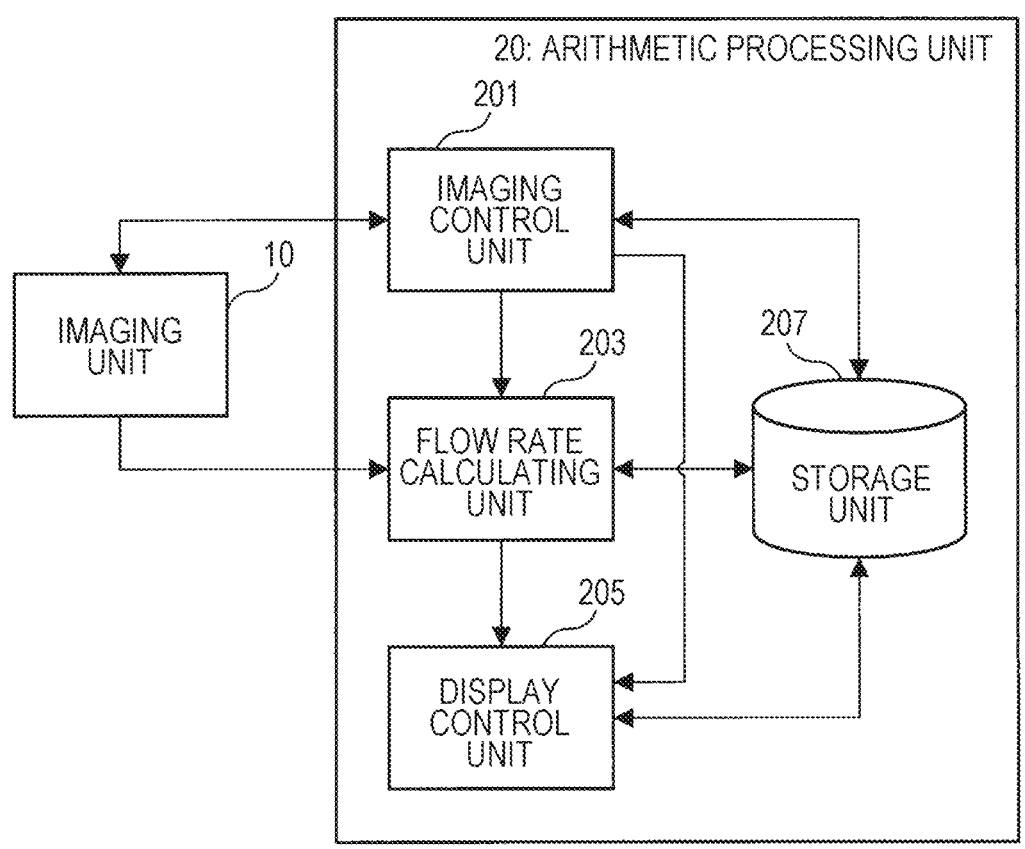
FIG. 16 is a block diagram schematically illustrating one example of the configuration of an arithmetic processing unit provided in the flow rate measuring device according to the same embodiment.
Figure 17:
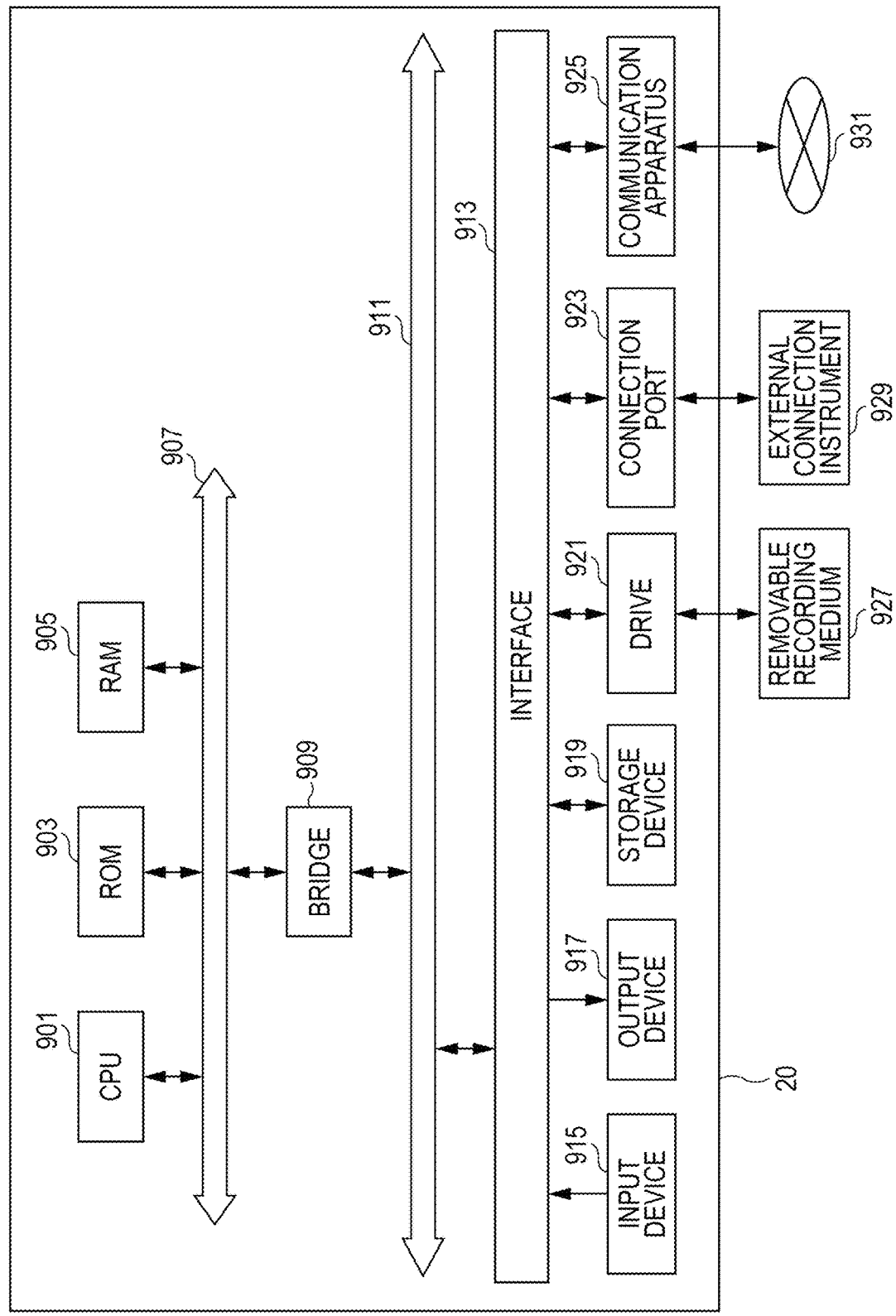
FIG. 17 is a block diagram schematically illustrating one example of the hardware configuration of the arithmetic processing unit provided in the flow rate measuring device according to the same embodiment.
Figure 18:
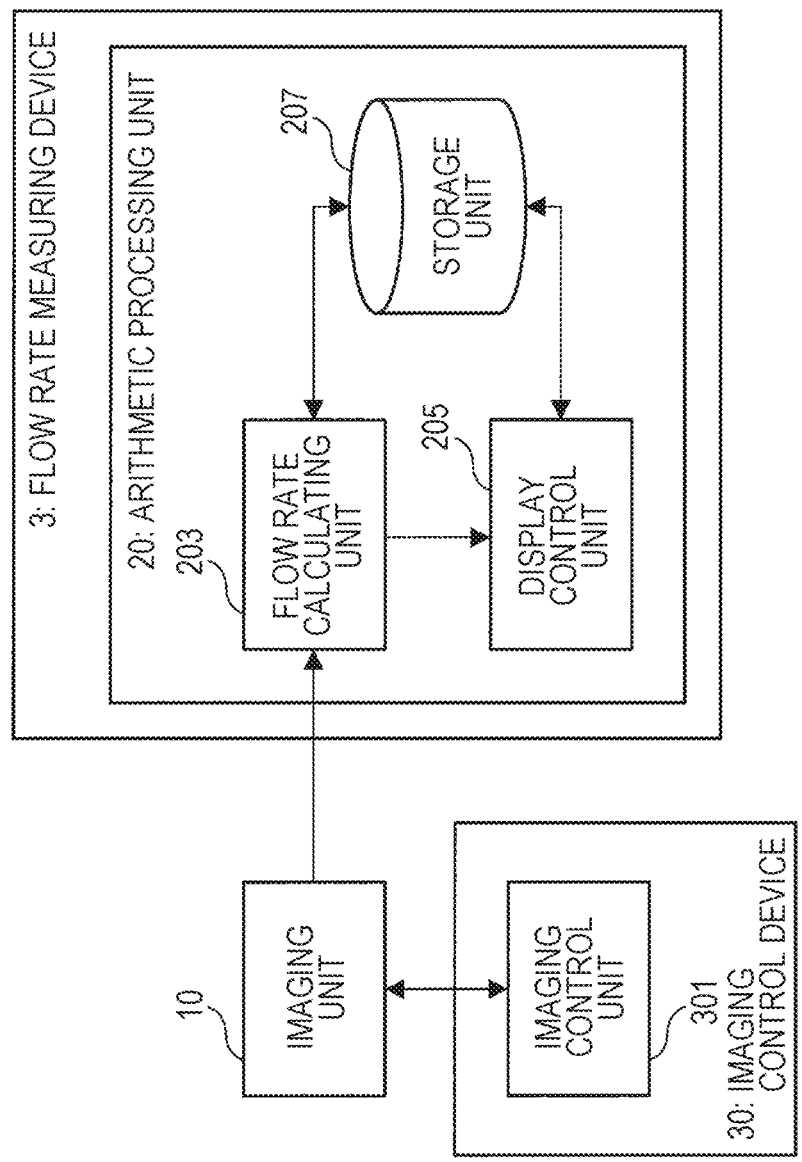
FIG. 18 is a block diagram schematically illustrating another example of the configuration of the flow rate measuring device according to the same embodiment.

FIG. 10 is a block diagram schematically illustrating one example of the configuration of the flow rate measuring device according to the embodiment. FIG. 11 is a block diagram schematically illustrating one example of the configuration of a laser light source provided in the flow rate measuring device according to the embodiment. FIG. 12 is a block diagram schematically illustrating one example of the configuration of an imaging device provided in the flow rate measuring device according to the embodiment. FIGS. 13A and 13B are explanatory views for illustrating a dove prism. FIG. 14 is an explanatory view for illustrating the flow rate measuring device according to the embodiment. FIG. 15 is a block diagram schematically illustrating another example of the configuration of an imaging device provided in the flow rate measuring device according to the embodiment. FIG. 16 is a block diagram schematically illustrating one example of the configuration of an arithmetic processing unit provided in the flow rate measuring device according to the embodiment. FIG. 17 is a block diagram schematically illustrating one example of the hardware configuration of the arithmetic processing unit provided in the flow rate measuring device according to the embodiment. FIG. 18 is a block diagram schematically illustrating another example of the configuration of flow rate measuring device according to the embodiment.

[Overall Configuration of Flow Rate Measuring Device 1]

As schematically illustrated in FIG. 10, a flow rate measuring device 1 according to the embodiment mainly includes an imaging unit 10 and an arithmetic processing unit 20.

The imaging unit 10 applies a predetermined wavelength of laser light as illumination light to light scattering fluid S under control of the arithmetic processing unit 20. Furthermore, the imaging unit 10 images a plurality of laser speckles, generated by the laser light, of the light scattering fluid under the above-described imaging condition as illustrated in FIG. to generate a plurality of speckle images. The imaging unit 10 outputs the plurality of generated speckle images to the arithmetic processing unit 20.

The detailed configuration of the above-described imaging unit 10 will be described below again.

The arithmetic processing unit 20 controls the imaging processing of the speckle image at the imaging unit 10. Furthermore, the arithmetic processing unit 20 calculates the flow rate (i.e., direction and speed of flow) of the light scattering fluid of interest by using the plurality of speckle images generated by the imaging unit 10.

The detailed configuration of the above-described arithmetic processing unit 20 will be described below again.

[Configuration of Imaging Unit 10]

As schematically illustrated in FIG. 10, the imaging unit 10 according to the embodiment includes a laser light source 101 and an imaging device 103.

Furthermore, in addition to the configuration as described above, the imaging unit 10 according to the embodiment may further include various mechanisms for obtaining at least one of, for example, a general speckle imaging image, a bright-field image, a fluorescence image, or a narrow band imaging (NBI) image. These images are used for specifying the position of a conduit such as a blood vessel and a lymph vessel. Furthermore, the configuration of the imaging unit 10 as described above may further include various functions for obtaining at least any one of, for example, the speckle imaging image, the bright-field image, the fluorescence image, or the NBI image. With this arrangement, a user of the flow rate measuring device 1 according to the embodiment can more easily specify the position of the light scattering fluid, whose flow rate is desired to be measured.

The laser light source 101 and the imaging device 103 according to the embodiment will be described in detail below.

Laser Light Source 101

The laser light source 101 applies laser light to the light scattering fluid S to be measured. Then, the light scattering fluid S randomly scatters the applied laser light, and a laser speckle pattern is generated. The wavelength of the laser light emitted from the laser light source 101 is not particularly limited, and any wavelength can be selected. Note that, in order to further improve measurement accuracy, the laser light preferably has a shorter wavelength. Furthermore, it is more preferable for the laser light emitted from the laser light source 101 to have higher coherence. Moreover, the laser light emitted from the laser light source 101 preferably has a longitudinal mode of single frequency and a transverse mode of $TEM_{00}$.

Note that, in order to illuminate a wider range of the light scattering fluid S, linear laser light is preferably applied to the light scattering fluid S. The linear laser light can be achieved by providing various optical elements, such as a rod lens and a Powell lens (line generator projection lens), on the downstream side of the laser light source 101 and making the laser light emitted from the laser light source 101 incident on these optical elements.

Examples of the laser light source 101 as described above include a semiconductor laser light source as schematically illustrated in FIG. 11. As schematically illustrated in FIG. 11, such a laser light source includes, for example, a laser diode 111, a collimator 113, an isolator 115, an anamorphic prism pair 117, a λ/2 wavelength plate 119, and a coupling port 121.

The laser light emitted from the laser diode 111 is transmitted through the collimator 113, and turns to collimated light. The collimated light enters the isolator 115. The collimated light that has transmitted through the isolator 115 is transmitted through the anamorphic prism pair 117. The beam shape of the collimated light is thereby formed to a predetermined shape. The λ/2 wavelength plate 119 controls the polarization direction of the collimated light. The laser light having the controlled beam shape and polarization direction is connected to an optical fiber OF via the coupling port 121, and guided to a measurement part of the light scattering fluid. Furthermore, the isolator 115 prevents reflected light of the laser light from the coupling port 121 from reaching the laser diode 111. The laser oscillation efficiency of the laser diode 111 is controlled so as not to be decreased.

The imaging unit 10 according to the embodiment can be smaller by using the semiconductor laser light source as illustrated in FIG. 11 as the laser light source 101.

Imaging Device 103

The imaging device 103 images a speckle pattern generated in the light scattering fluid S under a specific imaging condition as illustrated in FIG. 5 to generate at least two or more speckle images. Data of the at least two or more generated speckle images is output to the arithmetic processing unit 20.

Examples of the above-described imaging device 103 include an imaging device mounted with an area sensor. As schematically illustrated in FIG. 12, the imaging device mounted with an area sensor includes at least an imaging lens 131 and an area sensor 133, which is an imaging element. Furthermore, as illustrated in FIG. 7, a dove prism 135 is preferably provided on the upstream side of the imaging lens 131 so that the extending direction of a conduit (e.g., blood vessel, lymph vessel, and the like) through which light scattering fluid passes is overlapped with the scanning direction of the area sensor 133.

Here, the imaging lens 131 provided in the imaging device 103 is not particularly limited, and any lens can be used. Furthermore, although only one lens is illustrated as the imaging lens 131 in FIG. 12, the type and number of the optical element constituting the imaging lens 131 are not particularly limited, and a lens group including a plurality of optical elements may constitute the imaging lens 131.

Furthermore, the area sensor 133 is not particularly limited, and any area sensor utilizing, for example, charged-coupled devices (CCD) and a complementary metal-oxide-semiconductor (CMOS) can be used.

A high-speed frame rate can be achieved by using a part of pixel group as schematically illustrated in FIG. 6A among a plurality of pixels constituting the above-described area sensor 133. Imaging at the high-speed frame rate as illustrated in FIG. 5 can be achieved. The flow rate of the light scattering fluid is specified by analyzing speckle signals obtained from the specific pixel group.

Conduits (in particular, e.g., blood vessels and lymph vessels) through which light scattering fluid flows rarely extend parallel to the scanning direction (data reading direction) of the area sensor 133. In general, conduits often extend in any direction regardless of the scanning direction of the area sensor 133. Consequently, as illustrated in FIG. 7, the image formed on the area sensor 133 is rotated in a desired direction with the dove prism 135 so that the extending direction of a conduit is overlapped with the scanning direction of the area sensor 133.

As schematically illustrated in FIG. 13A, the dove prism 135 has a function of rotating light propagated along an optical axis of the dove prism 135 by 180 degrees. Furthermore, in a case where the dove prism 135 itself is rotated by θ degrees about the optical axis, the image transmitted through the dove prism 135 is rotated by 2θ degrees as schematically illustrated in FIG. 13B. Using the above-described dove prism 135 enables the extending direction of a conduit through which the light scattering fluid flows to be overlapped with the scanning direction of the area sensor 133. An image of the light scattering fluid is formed on the area sensor 133.

Note that, in order to achieve such adjustment of the extending direction, a guide indicating the scanning direction of the area sensor 133 is preferably displayed on a display screen referred to by the user of the flow rate measuring device 1, as schematically illustrated in FIG. 14. This enables the user of the flow rate measuring device 1 to easily control the rotation of the dove prism 135, and overlap the extending direction of a conduit through which light scattering fluid flows with the scanning direction of the area sensor 133. An image of the light scattering fluid is formed on the area sensor 133.

Furthermore, examples of another imaging device 103 according to the embodiment include an imaging device mounted with a line sensor. For example, as schematically illustrated in FIG. 15, the imaging device mounted with the line sensor includes the imaging lens 131, an optical lens 141, an area sensor 143, a line sensor 145, a half mirror HM, and a mirror M.

In such an imaging device, the half mirror HM is arranged on a Fourier plane of the imaging lens 131 with respect to an object. The half mirror HM branches a path of light that has entered the imaging lens 131 into a light path to the area sensor 143 and a light path to the line sensor 145. Furthermore, the optically equivalent optical lens 141 is provided between the half mirror HM and each sensor.

In such an imaging device, the area sensor 143 is provided as a mechanism for obtaining at least any one of, for example, a general speckle imaging image, a bright-field image, a fluorescence image, or an NBI image, which are used for specifying the position of a conduit such as a blood vessel and a lymph vessel. The image formed on the area sensor 143 is subject to processing such as speckle processing as appropriate, and provided to the user of the flow rate measuring device 1. The user of the flow rate measuring device 1 specifies the position of a conduit (e.g., blood vessel, lymph vessel, and the like) through which light scattering fluid flows by referring to such an image.

Furthermore, the line sensor 145 is provided at a position conjugate with the image position of the area sensor 143. The line sensor 145 is installed on a holding mechanism movable in X, Y, and θ directions in the plane thereof. In a similar manner in FIG. 14, such a holding mechanism enables the line sensor 145 to be moved to the position equivalent to the conduit position specified by the user of the flow rate measuring device 1. The flow rate of the light scattering fluid is specified by analyzing speckle signals obtained from the above-described line sensor 145.

The imaging unit 10 according to the embodiment has been described in detail above.

[Configuration of Arithmetic Processing Unit 20]

One example of the configuration of the arithmetic processing unit 20 according to the embodiment will now be described in detail with reference to FIG. 16.

As schematically illustrated in FIG. 16, the arithmetic processing unit 20 according to the embodiment mainly includes an imaging control unit 201, a flow rate calculating unit 203, a display control unit 205, and a storage unit 207.

The imaging control unit 201 is implemented by, for example, a central processing unit (CPU), a read only memory (ROM), a random access memory (RAM), a communication apparatus, and the like. The imaging control unit 201 is a processing unit that comprehensively controls imaging processing of speckle patterns at the imaging unit 10. The imaging control unit 201 controls the imaging unit 10 to adjust, for example, application timing of laser light and imaging conditions (exposure time ET, imaging interval Δt, and pixel position of sensor to be used) of the imaging device 103 to a desired state. This enables imaging at the high-speed frame rate as illustrated in FIG. 5.

Furthermore, the imaging control unit 201 can also provide the user of the flow rate measuring device 1 with information regarding, for example, imaging conditions set by the imaging unit 10 and, for example, various images obtained from the imaging unit 10 via the later-described display control unit 205.

The flow rate calculating unit 203 is implemented by, for example, a CPU, a ROM, a RAM, and the like. The flow rate calculating unit 203 calculates the flow rate (i.e., direction and speed of flow) of light scattering fluid of interest in the above-described method by using two or more speckle images obtained from the imaging unit 10. Furthermore, the flow rate calculating unit 203 according to the embodiment can perform various pieces of known preprocessing such as sensitivity correction of an image and dark level correction of an image prior to the flow rate calculating processing for light scattering fluid.

The flow rate calculating unit 203 provides the calculated information regarding the flow rate of the light scattering fluid to the user of the flow rate measuring device 1 via the later-described display control unit 205. Furthermore, the flow rate calculating unit 203 may provide information regarding the calculated flow rate of the light scattering fluid to the user of the flow rate measuring device 1 by outputting the information as voice.

The display control unit 205 is implemented by, for example, a CPU, a ROM, a RAM, an output device, and the like. The display control unit 205 performs display control in a case where various pieces of information regarding the imaging unit 10 output from the imaging control unit 201 and information regarding the flow rate of light scattering fluid output from the flow rate calculating unit 203 are displayed on, for example, an output device such as a display provided in the flow rate measuring device 1 or an output device provided outside the flow rate measuring device 1. With this arrangement, the user of the flow rate measuring device 1 can grasp, for example, information regarding the flow rate of the light scattering fluid on the spot.

The storage unit 207 is implemented by, for example, a RAM, a storage device, or the like provided in the arithmetic processing unit 20 according to the embodiment. For example, various parameters and progress of processing, which have need to be stored by the arithmetic processing unit 20 according to the embodiment during some sort of processing, or, for example, various databases and programs are appropriately stored in the storage unit 207. For example, the imaging control unit 201, the flow rate calculating unit 203, and the display control unit 205 can freely perform read/write processing of data in the storage unit 207.

One example of the functions of the arithmetic processing unit 20 according to the embodiment has been described above. Each of the above-described components may be configured with a general-purpose member and a circuit, or may be configured with hardware specialized in the function of each component. Furthermore, for example, a CPU may implement all the functions of each component. Consequently, the configuration to be used can be appropriately changed according to the technical levels at the times when the embodiment is carried out.

Note that a computer program for implementing each function of the arithmetic processing unit as described above according to the embodiment can be created, and mounted in, for example, a personal computer. Furthermore, a computer-readable recording medium in which such a computer program is stored can be provided. The recording medium includes, for example, a magnetic disk, an optical disk, a magneto-optical disk, a flash memory, and the like. Furthermore, the above-described computer program may be distributed via, for example, a network without using a recording medium.

[Hardware Configuration of Arithmetic Processing Unit 20]

The hardware configuration of the arithmetic processing unit 20 according to the embodiment of the present disclosure will now be described in detail with reference to FIG. 17. FIG. 17 is a block diagram for illustrating the hardware configuration of the arithmetic processing unit 20 according to the embodiment of the present disclosure.

The arithmetic processing unit 20 mainly includes a CPU 901, a ROM 903, and a RAM 905. Furthermore, the arithmetic processing unit 20 further includes a host bus 907, a bridge 909, an external bus 911, an interface 913, an input device 915, an output device 917, a storage device 919, a drive 921, a connection port 923, and a communication apparatus 925.

The CPU 901 functions as an arithmetic processing device and a control device. The CPU 901 controls overall or part of operation in the arithmetic processing unit 20 in accordance with various programs recorded in the ROM 903, the RAM 905, the storage device 919, or a removable recording medium 927. For example, programs and arithmetic parameters used by the CPU 901 are stored in the ROM 903. The RAM 905 primarily stores, for example, programs used by the CPU 901 and parameters that appropriately change in the execution of the programs. These components are connected to each other by the host bus 907 including an internal bus such as a CPU bus.

The host bus 907 is connected to the external bus 911 such as a peripheral component interconnect/interface (PCI) bus via the bridge 909.

For example, the input device 915 is operation means, such as a mouse, a keyboard, a touch panel, a button, a switch, and a lever, operated by a user. Furthermore, the input device 915 may include, for example, remote-control means (so-called remote) using infrared rays or other radio waves, or an external connection instrument 929 such as a mobile phone and a PDA to cope with operations of the arithmetic processing unit 20. Moreover, the input device 915 includes, for example, an input control circuit that generates an input signal on the basis of information input by the user using the above-described operation means and outputs the input signal to the CPU 901 and the like. The user of the arithmetic processing unit 20 can input various pieces of data to the arithmetic processing unit 20 and give an instruction to perform processing operation by operating the input device 915.

The output device 917 includes a device capable of visually or audibly notifying the user of the acquired information. Such a device includes display devices, voice output devices, printer devices, mobile phones, facsimiles, and the like. The display devices include CRT display devices, liquid crystal display devices, plasma display devices, EL display devices, lamps, and the like. The voice output devices include speakers, headphones, and the like. For example, the output device 917 outputs results obtained from various pieces of processing performed by the arithmetic processing unit 20. Specifically, the display device displays the results obtained from various pieces of processing performed by the arithmetic processing unit 20 in text or images. Meanwhile, the voice output device converts an audio signal to an analog signal, and outputs the signal. The audio signal includes, for example, reproduced voice data and acoustic data.

The storage device 919 is configured as one example of a storage unit of the arithmetic processing unit 20, and stores data. The storage device 919 includes, for example, a magnetic storage device such as a hard disk drive (HDD), a semiconductor storage device, an optical storage device, a magneto-optical storage device, or the like. The storage device 919 stores, for example, programs executed by the CPU 901, various pieces of data, and various pieces of data acquired from the outside.

The drive 921 is a reader/writer for a recording medium, and is incorporated in or externally mounted on the arithmetic processing unit 20. The drive 921 reads information recorded in the attached removable recording medium 927, and outputs the information to the RAM 905. The removable recording medium 927 includes, for example, a magnetic disk, an optical disk, a magneto-optical disk, and a semiconductor memory. Furthermore, the drive 921 can write a record in the attached removable recording medium 927 such as a magnetic disk, an optical disk, magneto-optical disk, and a semiconductor memory. The removable recording medium 927 includes, for example, a DVD medium, an HD-DVD medium, a Blu-ray (registered trademark) medium, and the like. Furthermore, the removable recording medium 927 may include, for example, a CompactFlash (CF) (registered trademark), a flash memory, and a secure digital (SD) memory card. Furthermore, the removable recording medium 927 may include, for example, an integrated circuit (IC) card having a non-contact type IC chip on board, an electronic appliance, and the like.

The connection port 923 is used for directly connecting an instrument to the arithmetic processing unit 20. Examples of the connection port 923 include a universal serial bus (USB) port, an IEEE 1394 port, a small computer system interface (SCSI) port, and the like. Other examples of the connection port 923 include an RS-232C port, an optical audio terminal, a High-Definition Multimedia Interface (HDMI) (registered trademark) port, and the like. The arithmetic processing unit 20 directly acquires various pieces of data from the external connection instrument 929, or provides various pieces of data to the external connection instrument 929 by connecting the external connection instrument 929 to the connection port 923.

The communication apparatus 925 is a communication interface including, for example, a communication device for connection to a communication network 931. The communication apparatus 925 includes, for example, a wired or wireless local area network (LAN), Bluetooth (registered trademark), a communication card for Wireless USB (WUSB), and the like. Furthermore, the communication apparatus 925 may include, for example, a router for optical communication, a router for an asymmetric digital subscriber line (ADSL), and a modem for various communications. The communication apparatus 925 can transmit and receive signals and the like, for example, on the Internet or to and from another communication instrument, for example, in accordance with a predetermined protocol such as TCP/IP. Furthermore, the communication network 931 connected to the communication apparatus 925 includes, for example, a network connected by wire or wireless. The communication network 931 may include, for example, the Internet, a home LAN, infrared communication, radio wave communication, satellite communication, and the like.

One example of the hardware configuration capable of implementing the functions of the arithmetic processing unit 20 according to the embodiment of the present disclosure has been described above. Each of the above-described components may include a general-purpose member or hardware specialized in the function of each component. Consequently, the hardware configuration to be used can be appropriately changed according to the technical levels at the times of carrying out the embodiment.

[Variation of Flow Rate Measuring Device]

The flow rate measuring device 1 as described above includes an imaging unit 10 and an arithmetic processing unit 20. A separate imaging unit 10 capable of imaging a speckle image under the imaging condition as illustrated in FIG. 5 is present as a variation of the flow rate measuring device according to the embodiment. A flow rate measuring device including the arithmetic processing unit 20, which performs flow rate calculating processing by using the speckle image acquired from the above-described imaging unit 10, can be achieved. A variation of the flow rate measuring device according to the embodiment will be briefly described below.

For example, as illustrated in FIG. 18, the above-described flow rate measuring device 3 acquires a speckle image from the imaging unit 10 provided outside, and performs flow rate calculating processing on the basis of the acquired speckle image. The above-described flow rate measuring device 3 includes the arithmetic processing unit 20 provided with the flow rate calculating unit 203, a display control unit 205, and a storage unit 207.

In the imaging unit 10 provided outside, an imaging control device 30 controls, for example, imaging conditions. The imaging control device 30 includes an imaging control unit 301 having functions similar to those of the imaging control unit 201 according to the embodiment.

The flow rate calculating unit 203 of the flow rate measuring device 3 acquires at least two or more speckle images from the imaging unit 10, and calculates the flow rate of light scattering fluid in a manner similar to that described above. Obtained information regarding the flow rate of the light scattering fluid is provided to a user of the flow rate measuring device 3 via the display control unit 205.

A variation of the flow rate measuring device according to the embodiment has been briefly described above with reference to FIG. 18.

EXAMPLE

The flow rate measuring method and the flow rate measuring device according to the present disclosure will then be specifically described with reference to examples. Note that the following examples are merely examples of the flow rate measuring method and the flow rate measuring device according to the present disclosure, and the flow rate measuring method and the flow rate measuring device according to the present disclosure are not limited to the following examples.

Example 1

In the example, the flow rate of blood was measured by using a pseudo blood vessel and animal blood flow in order to simulate a situation in which the flow state of blood is observed focusing on the blood vessel of a patient under an operation.

In the flow rate measuring device 1, a laser light source as illustrated in FIG. 11 was used as the laser light source 101 of the imaging unit 10. In such a laser light source, a semiconductor laser having a wavelength of 823 nm, an output of 150 mW, a transverse mode of $TEM_{00}$, and a longitudinal multimode was used as the laser diode 111. A beam was formed by the collimator 113 and the anamorphic prism pair 117. Laser light was introduced from the coupling port 121 to a single mode optical fiber. The laser light, which had been emitted from the optical fiber, entered a line generator projection lens so as to be linear illumination light, and was applied to a sample.

Figure 19:
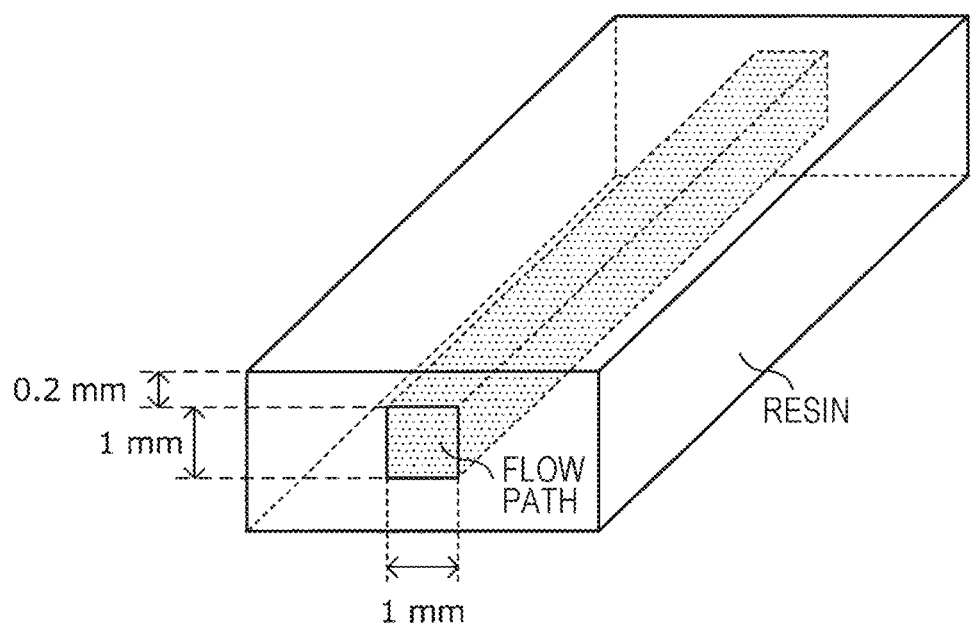
FIG. 19 is an explanatory view schematically illustrating the structure of a blood vessel phantom used in an example.

The flow rate of animal blood flowing through a flow path in a blood vessel phantom was measured by using the blood phantom as illustrated in FIG. 19. The blood vessel phantom illustrated in FIG. 19 includes resin having an equivalent scattering coefficient and an equivalent absorption coefficient that are designed to be equivalent to those of an inner wall of a human stomach. A flow path in which blood can flow is formed in the blood vessel phantom. The flow path is formed at a depth of 0.2 mm from an observation surface, and has a cross section of 1 mm×1 mm. Pig blood was flowed through the flow path by a pump at a speed of 1 mm/s to be observed. The observation was performed by applying laser light from the upper side of the blood vessel phantom and imaging the diffusely reflected light with the imaging device 103 disposed above.

A general camera lens was used as the imaging device 103. The imaging device 103 had a working distance of 200 mm, an F value of 8, and an image magnification of approximately 0.6. The imaging element in the imaging device 103 is a Bayer array rolling shutter type color CMOS sensor (area sensor) having a pixel size of 1.85 μm square and 2080×4096 effective pixels.

Known sensitivity correction processing and dark level correction processing were performed on a speckle image obtained from the imaging device 103, and the flow rate was calculated.

Note that, in the embodiment, only a pixel group positioned at 1024th line in the vertical direction of the area sensor was scanned by one line in a manner similar to those in FIGS. 6A and 7. With this arrangement, one-dimensional speckle image was continually acquired at a frame rate of 109.5 kHz.

Prior measurement had revealed that time until correlation between speckle patterns disappears (i.e., spatial correlation disappearance time) in the sample is to 100 μs. At the above-described frame rate, time shorter than the spatial correlation disappearance time is defined as exposure time, and continual imaging can be performed at a time interval shorter than the spatial correlation disappearance time.

Figure 20:
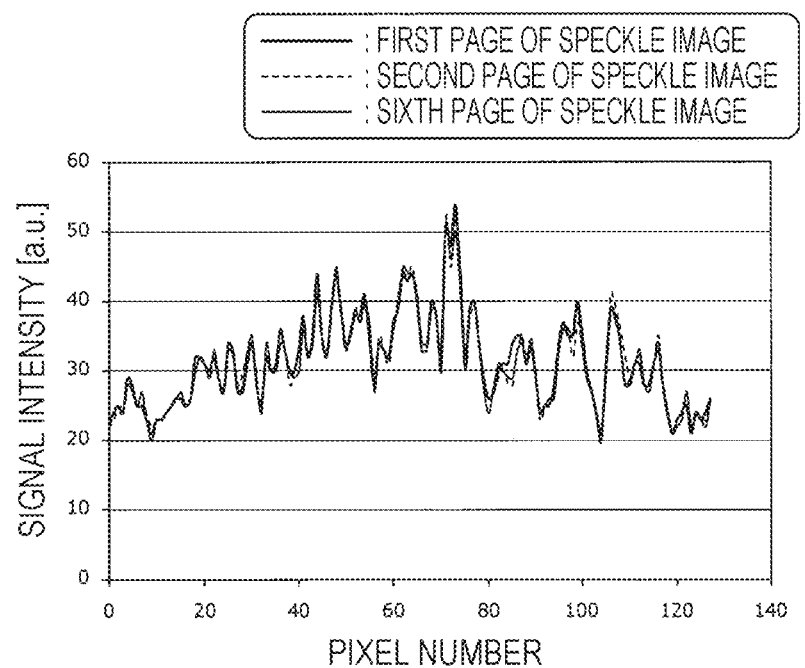
FIG. 20 is a graph for illustrating Example 1.

FIG. 20 together illustrates a speckle image signal at a flow path position of the first frame, a speckle image signal of the second frame, and a speckle image signal of the sixth frame, which are acquired by such measurement. In FIG. 20, the horizontal axis indicates the pixel number. Blood flows from left to right (i.e., from small pixel number side to large pixel number side).

Figure 21:
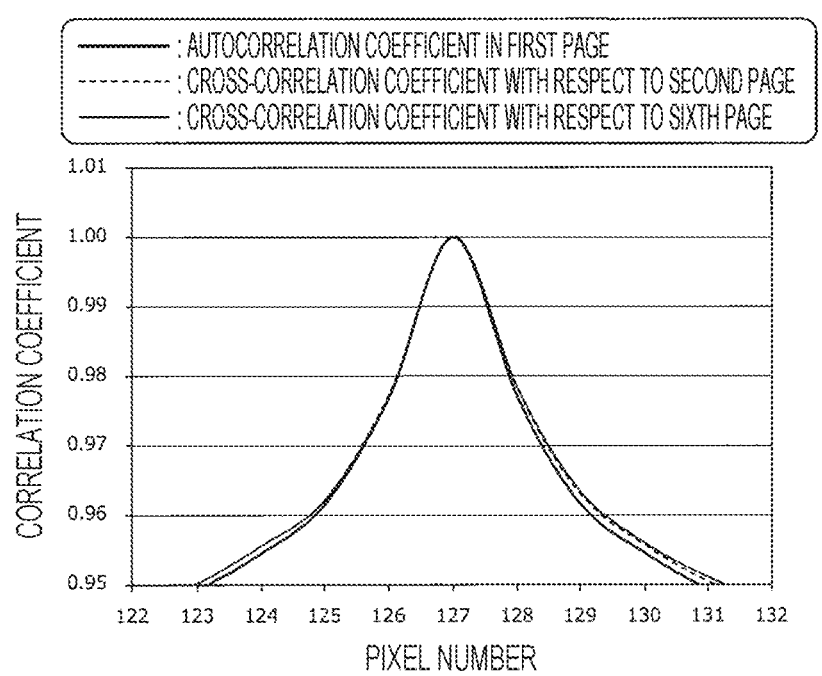
FIG. 21 is a graph for illustrating Example 1.

The speckle image signals of the second frame and the sixth frame correspond to light intensity signals in the blood flow direction respectively imaged after 9.13 microseconds and 45.7 microseconds, with the imaging timing of the first frame defined as a standard. FIG. 21 illustrates a result obtained by calculating an autocorrelation coefficient of the speckle image of the first frame and a cross-correlation coefficient between the speckle image of the first frame and the speckle image of the second or sixth frame. Identification of a direction of blood flow from raw data, on a speckle image signal, illustrated in FIG. 20 is difficult. In a case where attention is paid to the plot of the correlation coefficient illustrated in FIG. 21, the peak position of the correlation coefficient is found to slightly move in the flow direction with respect to the pixel position of the horizontal axis.

Such a result reveals that blood flows in the direction from small to large pixel number side. The obtained speed of blood flow was 16.7 mm/s.

Example 2

Also, in the example, the flow rate of blood is measured by using a pseudo blood vessel and animal blood flow in order to simulate a situation in which the flow state of blood is observed focusing on the blood vessel of a patient under an operation.

In the flow rate measuring device 1, an external resonance semiconductor laser having a wavelength of 800 nm, an output of 200 mW, a transverse mode of $TEM_{00}$, and a longitudinal mode of single frequency was used as the laser light source 101 of the imaging unit 10. A beam was formed by a beam expander to be applied to a sample by a projection lens.

A sample similar to that in Example 1 was used. Pig blood was flowed through the formed flow path by the pump at a speed of 1 mm/s to be observed. The observation was performed by applying laser light from the upper side of the blood vessel phantom and imaging the diffusely reflected light with the imaging device disposed above.

A general camera lens was used as the imaging device 103. The imaging device 103 had a working distance of 200 mm, an F value of 8, and an image magnification of approximately 0.6. The imaging element in the imaging device 103 is a Bayer array rolling shutter type color CMOS sensor (area sensor) having a pixel size of 1.85 μm square and 2080×4096 effective pixels.

Figure 22:
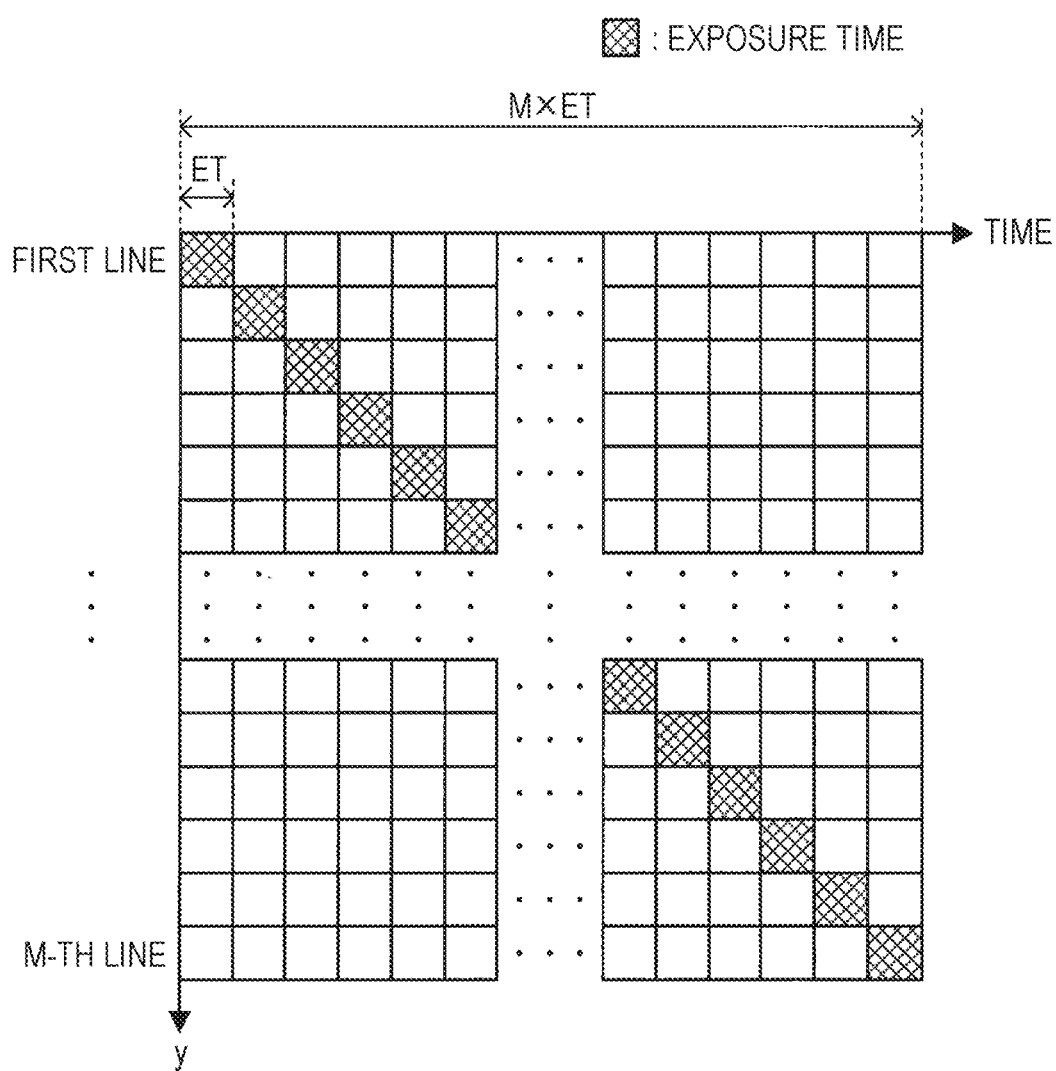
FIG. 22 is an explanatory view for illustrating Example 2.

In the example, as illustrated in FIG. 22, a two-dimensional speckle image was acquired by performing exposure for only 9.13 microseconds every 9.13 microseconds (i.e., ET=Δt=9.13 μs) by one line in the vertical direction. In FIG. 22, the vertical axis represents the number of horizontal pixel lines to be exposed in the vertical direction, and the horizontal axis represents time. The hatched rectangles in the drawing indicate exposure time.

Known sensitivity correction processing and dark level correction processing were performed on a speckle image obtained from the imaging device 103, and the cross-correlation coefficient of a signal profile in the horizontal direction was calculated for each of the adjacent lines.

Figure 23:
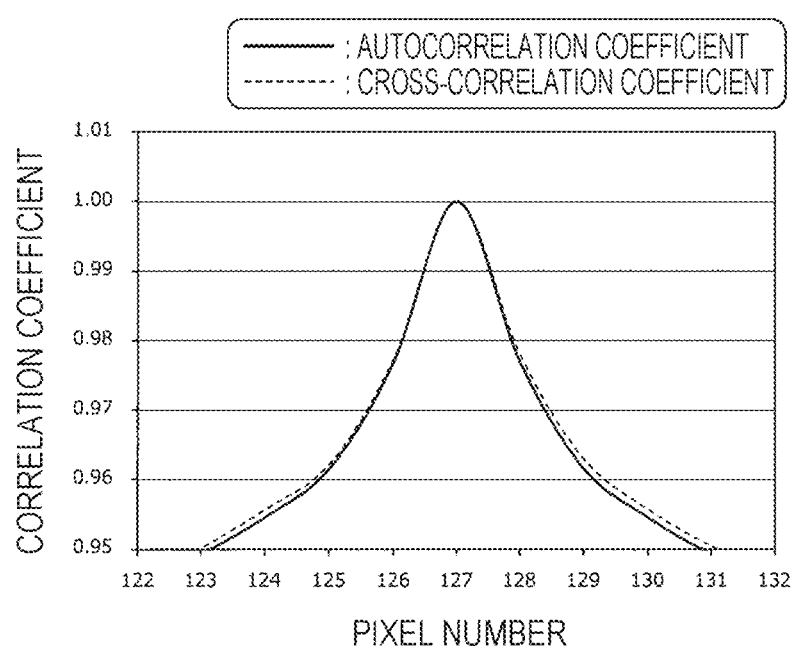
FIG. 23 is a graph for illustrating Example 2.

FIG. 23 illustrates each of the autocorrelation coefficient of the signal profile of the 1024th line and the cross-correlation coefficient between the signal profile of the 1024th line and the signal profile of the 1025th line. As illustrated in FIG. 23, the peak position of the correlation coefficient is found to slightly move in the flow direction with respect to the pixel position of the horizontal axis.

Such a result reveals that blood flows in the direction from small to large pixel number side. The obtained speed of blood flow was 16.7 mm/s.

Although the preferred embodiment of the present disclosure has been described in detail above with reference to the accompanying drawings, the technical scope of the present disclosure is not limited to such an example. It is apparent that a person having ordinary skill in the art of the present disclosure can arrive at various alternations or modifications within the scope of the technical ideas set forth in the claims. These alternations or modifications are understood to naturally fall within the technical scope of the present disclosure.

Furthermore, the effects described herein are merely illustrative or exemplary, and not limitative. That is, the technique according to the present disclosure may have other effects that are obvious to a skilled person from the description of the present specification, together with or in place of the above-described effects.

Note that, the configurations as described below also fall within the technical scope of the present disclosure.

(1)
A flow rate measuring method including:
generating two or more speckle images by continually imaging light scattering fluid to be measured, while defining time shorter than spatial correlation disappearance time corresponding to time in which spatial correlation between speckle patterns generated by the light scattering fluid disappears as exposure time, at a time interval shorter than the spatial correlation disappearance time; and
calculating direction and speed of flow of the light scattering fluid from time variation of the speckle patterns between the two or more speckle images,
in which the speckle images are imaged by using an imaging device mounted with an area sensor and a pixel group of a part of the area sensor or by using an imaging device mounted with a line sensor.

(2)
The flow rate measuring method according to (1),
in which the light scattering fluid moves inside a conduit extending in a predetermined direction, and
the speckle images are imaged with a scanning direction of a sensor used for imaging being largely overlapped with an extending direction of the conduit.

(3)
The flow rate measuring method according to (1) or (2),
in which cross-correlation, which is calculated by using the two or more speckle images, between spatial distributions of speckle images is used as an index representing time variation of the speckle patterns accompanying movement of the light scattering fluid, and
direction and speed of flow of the light scattering fluid is calculated on the basis of the cross-correlation between spatial distributions of speckle images.

(4)
The flow rate measuring method according to (3),
in which speed of the light scattering fluid is calculated, while defining a shift direction of a peak value of the cross-correlation between spatial distributions of speckle images as a flow direction of the light scattering fluid, on the basis of a shift amount of the peak value, a size of a pixel in the sensor, and the time interval.

(5)
The flow rate measuring method according to any one of (1) to (4), in which the light scattering fluid is linearly illuminated with laser light emitted from a laser light source.

(6)
The flow rate measuring method according to any one of (1) to (5), in which the light scattering fluid includes blood or body fluid flowing in a living body.

(7)
A flow rate measuring device including:
a laser light source configured to apply a predetermined wavelength of laser light to light scattering fluid to be measured;
an imaging device configured to generate two or more speckle images by continually imaging the light scattering fluid, while defining time shorter than spatial correlation disappearance time corresponding to time in which spatial correlation between speckle patterns generated by the light scattering fluid disappears as exposure time, at a time interval shorter than the spatial correlation disappearance time; and
an arithmetic processing unit configured to calculate direction and speed of flow of the light scattering fluid from time variation of the speckle patterns between the two or more speckle images,
in which the speckle images are imaged by using an imaging device mounted with an area sensor as the imaging device and a pixel group of a part of the area sensor or by using an imaging device mounted with a line sensor as the imaging device.

(8)
A flow rate measuring device including an arithmetic processing unit configured to calculate direction and speed of flow of light scattering fluid from time variation of speckle patterns between two or more speckle images by using the two or more speckle images generated by continually imaging the light scattering fluid to be measured on which a predetermined wavelength of laser light is applied, while defining time shorter than spatial correlation disappearance time corresponding to time in which spatial correlation between the speckle patterns generated by the light scattering fluid disappears as exposure time, at a time interval shorter than the spatial correlation disappearance time,
in which the arithmetic processing unit uses objects, as the two or more speckle images, imaged by using an imaging device mounted with an area sensor and a pixel group of a part of the area sensor or by using an imaging device mounted with a line sensor.

(9)
A program causing a computer to implement an arithmetic processing function of calculating direction and speed of flow of light scattering fluid from time variation of speckle patterns between two or more speckle images by using the two or more speckle images generated by continually imaging light scattering fluid to be measured on which a predetermined wavelength of laser light is applied, while defining time shorter than spatial correlation disappearance time corresponding to time in which spatial correlation between the speckle patterns generated by the light scattering fluid disappears as exposure time, at a time interval shorter than the spatial correlation disappearance time,
in which the arithmetic processing function uses objects, as the two or more speckle images, imaged by using an imaging device mounted with an area sensor and a pixel group of a part of the area sensor or by using an imaging device mounted with a line sensor.

REFERENCE SIGNS LIST 1, 3 Flow rate measuring device
10 Imaging unit
20 Arithmetic processing unit
30 Imaging control device
101 Laser light source
103 Imaging device
111 Laser diode
113 Collimator
115 Isolator
117 Anamorphic prism pair
119 $\lambda/2$ wavelength plate
121 Coupling port
131 Imaging lens
133, 143 Area sensor
135 Dove prism
141 Optical lens
145 Line sensor
201, 301 Imaging control unit
203 Flow rate calculating unit
205 Display control unit
207 Storage unit

The invention claimed is:

1. A flow rate measuring method comprising:
generating two or more speckle images by continually imaging light scattering fluid to be measured, while defining time shorter than spatial correlation disappearance time corresponding to time in which spatial correlation between speckle patterns generated by the light scattering fluid disappears as exposure time, at a time interval shorter than the spatial correlation disappearance time; and
calculating direction and speed of flow of the light scattering fluid from time variation of the speckle patterns between the two or more speckle images,
wherein the speckle images are imaged by using an imaging device mounted with an area sensor and a pixel group of a part of the area sensor or by using an imaging device mounted with a line sensor.

2. The flow rate measuring method according to claim 1, wherein the light scattering fluid moves inside a conduit extending in a predetermined direction, and
the speckle images are imaged with a scanning direction of a sensor used for imaging being largely overlapped with an extending direction of the conduit.

3. The flow rate measuring method according to claim 1, wherein cross-correlation, which is calculated by using the two or more speckle images, between spatial distributions of speckle images is used as an index representing time variation of the speckle patterns accompanying movement of the light scattering fluid, and
direction and speed of flow of the light scattering fluid is calculated on a basis of the cross-correlation between spatial distributions of speckle images.

4. The flow rate measuring method according to claim 3, wherein speed of the light scattering fluid is calculated, while defining a shift direction of a peak value of the cross-correlation between spatial distributions of speckle images as a flow direction of the light scattering fluid, on a basis of a shift amount of the peak value, a size of a pixel in the sensor, and the time interval.

5. The flow rate measuring method according to claim 1, wherein the light scattering fluid is linearly illuminated with laser light emitted from a laser light source.

6. The flow rate measuring method according to claim 1, wherein the light scattering fluid includes blood or body fluid flowing in a living body.

7. A flow rate measuring device comprising:
a laser light source configured to apply a predetermined wavelength of laser light to light scattering fluid to be measured;
an imaging device configured to generate two or more speckle images by continually imaging the light scattering fluid, while defining time shorter than spatial correlation disappearance time corresponding to time in which spatial correlation between speckle patterns generated by the light scattering fluid disappears as exposure time, at a time interval shorter than the spatial correlation disappearance time; and
an arithmetic processing unit configured to calculate direction and speed of flow of the light scattering fluid from time variation of the speckle patterns between the two or more speckle images,
wherein the speckle images are imaged by using an imaging device mounted with an area sensor as the imaging device and a pixel group of a part of the area sensor or by using an imaging device mounted with a line sensor as the imaging device.

8. A flow rate measuring device comprising an arithmetic processing unit configured to calculate direction and speed of flow of light scattering fluid from time variation of speckle patterns between two or more speckle images by using the two or more speckle images generated by continually imaging the light scattering fluid to be measured on which a predetermined wavelength of laser light is applied, while defining time shorter than spatial correlation disappearance time corresponding to time in which spatial correlation between the speckle patterns generated by the light scattering fluid disappears as exposure time, at a time interval shorter than the spatial correlation disappearance time,
wherein the arithmetic processing unit uses objects, as the two or more speckle images, imaged by using an imaging device mounted with an area sensor and a pixel group of a part of the area sensor or by using an imaging device mounted with a line sensor.

9. A program causing a computer to implement an arithmetic processing function of calculating direction and speed of flow of light scattering fluid from time variation of speckle patterns between two or more speckle images by using the two or more speckle images generated by continually imaging light scattering fluid to be measured on which a predetermined wavelength of laser light is applied, while defining time shorter than spatial correlation disappearance time corresponding to time in which spatial correlation between the speckle patterns generated by the light scattering fluid disappears as exposure time, at a time interval shorter than the spatial correlation disappearance time,
wherein the arithmetic processing function uses objects, as the two or more speckle images, imaged by using an imaging device mounted with an area sensor and a pixel group of a part of the area sensor or by using an imaging device mounted with a line sensor.

* * * * *